US012735486B2

(12) United States Patent
Zong et al.

(10) Patent No.: US 12,735,486 B2
(45) Date of Patent: Sep. 15, 2026

(54) MULTIVALENT PROTEIN COMPLEXES

(71) Applicant: GUANGZHOU BINDING TECHNOLOGIES CO., LIMITED, Guangzhou (CN)

(72) Inventors: Yinong Zong, San Diego, CA (US); Yang Liu, San Diego, CA (US)

(73) Assignee: GUANGZHOU BINDING TECHNOLOGIES CO., LIMITED, Guangzhou (CN)

(*) Notice: Subject to any disclaimer, the term of this patent is extended or adjusted under 35 U.S.C. 154(b) by 521 days.

(21) Appl. No.: 17/057,450

(22) PCT Filed: May 20, 2019

(86) PCT No.: PCT/US2019/033079

§ 371 (c)(1),
(2) Date: Nov. 20, 2020

(87) PCT Pub. No.: WO2019/226529

PCT Pub. Date: Nov. 28, 2019

(65) Prior Publication Data

US 2021/0206857 A1 Jul. 8, 2021

Related U.S. Application Data

(60) Provisional application No. 62/674,375, filed on May 21, 2018.

(51) Int. Cl.

*C07K 16/28* (2006.01)
*C07K 16/46* (2006.01)
*A61K 39/00* (2006.01)

(52) U.S. Cl.

CPC ...... *C07K 16/2818* (2013.01); *C07K 16/2809* (2013.01); *C07K 16/2878* (2013.01); *C07K 16/2896* (2013.01); *C07K 16/468* (2013.01); *A61K 2039/505* (2013.01); *C07K 2317/52* (2013.01)

(58) Field of Classification Search

None
See application file for complete search history.

(56) References Cited

U.S. PATENT DOCUMENTS

| | | | |
|---|---|---|---|
| 6,013,763 A * | 1/2000 | Braisted | C07K 14/31 530/324 |
| 6,524,572 B1 * | 2/2003 | Li | C07K 14/705 435/235.1 |
| 7,572,631 B2 | 8/2009 | Berenson et al. | |
| 2007/0036783 A1 | 2/2007 | Humeau et al. | |
| 2015/0266939 A1 | 9/2015 | Vogan et al. | |
| 2016/0068811 A1 | 3/2016 | Kokaji | |
| 2016/0280744 A1 | 9/2016 | Honda et al. | |
| 2017/0306037 A1 | 10/2017 | Brogdon et al. | |

FOREIGN PATENT DOCUMENTS

| | | | |
|---|---|---|---|
| CN | 101107009 A | 1/2008 | |
| CN | 101124245 A | 2/2008 | |
| CN | 102939303 A | 2/2013 | |
| CN | 103635490 A | 3/2014 | |
| CN | 106414724 A | 2/2017 | |
| WO | WO-2015166049 A1 * | 11/2015 | C07K 16/28 |
| WO | WO-2016183387 A1 * | 11/2016 | A61K 47/6851 |
| WO | WO 2017/054033 | 4/2017 | |
| WO | WO-2017180913 A2 * | 10/2017 | A61P 35/00 |
| WO | WO-2018001985 A1 * | 1/2018 | C07K 14/70539 |
| WO | WO 2018/129397 | 7/2018 | |
| WO | WO 2019/023811 | 2/2019 | |

OTHER PUBLICATIONS

Trickett et al (JIM, 275:251-255, 2003.*
Moks et al (EJB, 156, 637-643, 1986).*
Eliasson et al (Jour. Imm., 142(2):575-581, 1989).*
Yonezawa et al (Clin. Cancer Res., 21(14):3113-20, 2015).*
Choe et al., "Fc-binding ligands of immunoglobulin G: an overview of high affinity proteins and peptides," Materials, Dec. 2016, 9(12):994.
Ito et al., "Development of an artificial antibody system with multiple valency using an Fv fragment fused to a fragment of protein A," Journal of Biological Chemistry, Sep. 25, 1993, 268(27):20668-75.
PCT International Preliminary Report on Patentability in International Appln. No. PCT/US2019/033079, dated Nov. 24, 2020, 8 pages.
PCT International Search Report and Written Opinion in International Appln. No. PCT/US2019/033079, dated Aug. 30, 2019, 10 pages.
Smith-Garvin et al., "T cell activation," Annual Review of Immunology, Apr. 23, 2009, 27:591, 31 pages.

* cited by examiner

*Primary Examiner* — Brad Duffy
(74) *Attorney, Agent, or Firm* — METIS IP LLC

(57) ABSTRACT

This disclosure is related to methods of making and using a multi-protein complex. The complex can create a multivalent binding mechanism for multiple targets in a solution or on a surface. The complex has various applications, and can be used, e.g., for activation and/or expansion of T cells.

4 Claims, 11 Drawing Sheets

Specification includes a Sequence Listing.

FIG.10

SEQ ID NO: 1
LENGTH: 58
ORGANISM: Staphylococcus aureus

ADNKFNKEQQNAFYEILHLPNLTEEQRNGFIQSLKDDPSVSKEILAEAKKLNDAQAPK

SEQ ID NO: 2
LENGTH: 60
ORGANISM: Staphylococcus aureus

AANAAQHDEAQQNAFYQVLNMPNLNADQRNGFIQSLKDDPSQSANVLGEAQKLNDSQAPK

SEQ ID NO: 3
LENGTH: 61
ORGANISM: Staphylococcus aureus

ADAQQNNFNKDQQSAFYEILNMPNLNEAQRNGFIQSLKDDPSQSTNVLGEAKKLNESQAPK

SEQ ID NO: 4
LENGTH: 58
ORGANISM: Staphylococcus aureus

ADNNFNKEQQNAFYEILNMPNLNEEQRNGFIQSLKDDPSQSANLLSEAKKLNESQAPK

SEQ ID NO: 5
LENGTH: 58
ORGANISM: Staphylococcus aureus

ADNKFNKEQQNAFYEILHLPNLNEEQRNGFIQSLKDDPSQSANLLAEAKKLNDAQAPK

SEQ ID NO: 6
LENGTH: 58
Artificial Sequence

VDNKFNKEQQNAFYEILHLPNLNEEQRNAFIQSLKDDPSQSANLLAEAKKLNDAQAPK

SEQ ID NO: 7
LENGTH: 55
ORGANISM: Streptococcus sp.

TYKLILNGKTLKGETTTEAVDAATAEKVFKQYANDNGVDGEWTYDDATKTFTVTE

SEQ ID NO: 8
LENGTH: 55
ORGANISM: Streptococcus sp.

TYKLVINGKTLKGETTTEAVDAATAEKVFKQYANDNGVDGEWTYDDATKTFTVTE

SEQ ID NO: 9
LENGTH: 55
ORGANISM: Streptococcus sp.

TYKLVINGKTLKGETTTKAVDAETAEKAFKQYANDNGVDGVWTYDDATKTFTVTE

SEQ ID NO: 10
LENGTH: 298
Artificial Sequence

Val Asp Asn Lys Phe Asn Lys Glu Gln Gln Asn Ala Phe Tyr Glu Ile Leu His Leu Pro
Asn Leu Asn Glu Glu Gln Arg Asn Ala Phe Ile Gln Ser Leu Lys Asp Asp Pro Ser Gln
Ser Ala Asn Leu Leu Ala Glu Ala Lys Lys Leu Asn Asp Ala Gln Ala Pro Lys Val Asp
Asn Lys Phe Asn Lys Glu Gln Gln Asn Ala Phe Tyr Glu Ile Leu His Leu Pro Asn Leu
Asn Glu Glu Gln Arg Asn Ala Phe Ile Gln Ser Leu Lys Asp Asp Pro Ser Gln Ser Ala
Asn Leu Leu Ala Glu Ala Lys Lys Leu Asn Asp Ala Gln Ala Pro Lys Val Asp Asn Lys

Fig. 10. Cont.

Phe Asn Lys Glu Gln Gln Asn Ala Phe Tyr Glu Ile Leu His Leu Pro Asn Leu Asn Glu
Glu Gln Arg Asn Ala Phe Ile Gln Ser Leu Lys Asp Asp Pro Ser Gln Ser Ala Asn Leu
Leu Ala Glu Ala Lys Lys Leu Asn Asp Ala Gln Ala Pro Lys Val Asp Asn Lys Phe Asn
Lys Glu Gln Gln Asn Ala Phe Tyr Glu Ile Leu His Leu Pro Asn Leu Asn Glu Glu Gln
Arg Asn Ala Phe Ile Gln Ser Leu Lys Asp Asp Pro Ser Gln Ser Ala Asn Leu Leu Ala
Glu Ala Lys Lys Leu Asn Asp Ala Gln Ala Pro Lys Val Asp Asn Lys Phe Asn Lys Glu
Gln Gln Asn Ala Phe Tyr Glu Ile Leu His Leu Pro Asn Leu Asn Glu Glu Gln Arg Asn
Ala Phe Ile Gln Ser Leu Lys Asp Asp Pro Ser Gln Ser Ala Asn Leu Leu Ala Glu Ala
Lys Lys Leu Asn Asp Ala Gln Ala Pro Lys His His His His His His His Cys

SEQ ID NO: 11
LENGTH: 6
Artificial Sequence

Gly Gly Gly Gly Gly Gly

SEQ ID NO: 12
LENGTH: 6
Artificial Sequence

Gly Ser Gly Ser Gly Ser

SEQ ID NO: 13
LENGTH: 5
Artificial Sequence

Ser Ser Ser Ser Ser

Fig. 10 Cont.

SEQUENCE LISTING

```
<160> NUMBER OF SEQ ID NOS: 13

<210> SEQ ID NO 1
<211> LENGTH: 58
<212> TYPE: PRT
<213> ORGANISM: Staphylococcus aureus

<400> SEQUENCE: 1

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
```

```
    50                  55


<210> SEQ ID NO 2
<211> LENGTH: 60
<212> TYPE: PRT
<213> ORGANISM: Staphylococcus aureus

<400> SEQUENCE: 2

Ala Ala Asn Ala Ala Gln His Asp Glu Ala Gln Gln Asn Ala Phe Tyr
1               5                   10                  15

Gln Val Leu Asn Met Pro Asn Leu Asn Ala Asp Gln Arg Asn Gly Phe
            20                  25                  30

Ile Gln Ser Leu Lys Asp Asp Pro Ser Gln Ser Ala Asn Val Leu Gly
        35                  40                  45

Glu Ala Gln Lys Leu Asn Asp Ser Gln Ala Pro Lys
    50                  55                  60


<210> SEQ ID NO 3
<211> LENGTH: 61
<212> TYPE: PRT
<213> ORGANISM: Staphylococcus aureus

<400> SEQUENCE: 3

Ala Asp Ala Gln Gln Asn Asn Phe Asn Lys Asp Gln Gln Ser Ala Phe
1               5                   10                  15

Tyr Glu Ile Leu Asn Met Pro Asn Leu Asn Glu Ala Gln Arg Asn Gly
            20                  25                  30

Phe Ile Gln Ser Leu Lys Asp Asp Pro Ser Gln Ser Thr Asn Val Leu
        35                  40                  45

Gly Glu Ala Lys Lys Leu Asn Glu Ser Gln Ala Pro Lys
    50                  55                  60


<210> SEQ ID NO 4
<211> LENGTH: 58
<212> TYPE: PRT
<213> ORGANISM: Staphylococcus aureus

<400> SEQUENCE: 4

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
        35                  40                  45

Lys Lys Leu Asn Glu Ser Gln Ala Pro Lys
    50                  55


<210> SEQ ID NO 5
<211> LENGTH: 58
<212> TYPE: PRT
<213> ORGANISM: Staphylococcus aureus

<400> SEQUENCE: 5

Ala Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ala Glu Ala
        35                  40                  45
```

-continued

Lys Lys Leu Asn Asp Ala Gln Ala Pro Lys
    50                  55

<210> SEQ ID NO 6
<211> LENGTH: 58
<212> TYPE: PRT
<213> ORGANISM: Artificial Sequence
<220> FEATURE:
<223> OTHER INFORMATION: Z domain (B domain of Protein A with mutations)

<400> SEQUENCE: 6

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 7
<211> LENGTH: 55
<212> TYPE: PRT
<213> ORGANISM: Streptococcus sp.

<400> SEQUENCE: 7

Thr Tyr Lys Leu Ile Leu Asn Gly Lys Thr Leu Lys Gly Glu Thr Thr
1               5                   10                  15

Thr Glu Ala Val Asp Ala Ala Thr Ala Glu Lys Val Phe Lys Gln Tyr
            20                  25                  30

Ala Asn Asp Asn Gly Val Asp Gly Glu Trp Thr Tyr Asp Asp Ala Thr
        35                  40                  45

Lys Thr Phe Thr Val Thr Glu
    50                  55

<210> SEQ ID NO 8
<211> LENGTH: 55
<212> TYPE: PRT
<213> ORGANISM: Streptococcus sp.

<400> SEQUENCE: 8

Thr Tyr Lys Leu Val Ile Asn Gly Lys Thr Leu Lys Gly Glu Thr Thr
1               5                   10                  15

Thr Glu Ala Val Asp Ala Ala Thr Ala Glu Lys Val Phe Lys Gln Tyr
            20                  25                  30

Ala Asn Asp Asn Gly Val Asp Gly Glu Trp Thr Tyr Asp Asp Ala Thr
        35                  40                  45

Lys Thr Phe Thr Val Thr Glu
    50                  55

<210> SEQ ID NO 9
<211> LENGTH: 55
<212> TYPE: PRT
<213> ORGANISM: Streptococcus sp.

<400> SEQUENCE: 9

Thr Tyr Lys Leu Val Ile Asn Gly Lys Thr Leu Lys Gly Glu Thr Thr
1               5                   10                  15

Thr Lys Ala Val Asp Ala Glu Thr Ala Glu Lys Ala Phe Lys Gln Tyr
            20                  25                  30

```
Ala Asn Asp Asn Gly Val Asp Gly Val Trp Thr Tyr Asp Asp Ala Thr
        35                  40                  45

Lys Thr Phe Thr Val Thr Glu
    50                  55


<210> SEQ ID NO 10
<211> LENGTH: 298
<212> TYPE: PRT
<213> ORGANISM: Artificial Sequence
<220> FEATURE:
<223> OTHER INFORMATION: Five tandemly connected Z domains

<400> SEQUENCE: 10

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys Val Asp Asn Lys Phe Asn
    50                  55                  60

Lys Glu Gln Gln Asn Ala Phe Tyr Glu Ile Leu His Leu Pro Asn Leu
65                  70                  75                  80

Asn Glu Glu Gln Arg Asn Ala Phe Ile Gln Ser Leu Lys Asp Asp Pro
                85                  90                  95

Ser Gln Ser Ala Asn Leu Leu Ala Glu Ala Lys Lys Leu Asn Asp Ala
            100                 105                 110

Gln Ala Pro Lys Val Asp Asn Lys Phe Asn Lys Glu Gln Gln Asn Ala
        115                 120                 125

Phe Tyr Glu Ile Leu His Leu Pro Asn Leu Asn Glu Glu Gln Arg Asn
    130                 135                 140

Ala Phe Ile Gln Ser Leu Lys Asp Asp Pro Ser Gln Ser Ala Asn Leu
145                 150                 155                 160

Leu Ala Glu Ala Lys Lys Leu Asn Asp Ala Gln Ala Pro Lys Val Asp
                165                 170                 175

Asn Lys Phe Asn Lys Glu Gln Gln Asn Ala Phe Tyr Glu Ile Leu His
            180                 185                 190

Leu Pro Asn Leu Asn Glu Glu Gln Arg Asn Ala Phe Ile Gln Ser Leu
        195                 200                 205

Lys Asp Asp Pro Ser Gln Ser Ala Asn Leu Leu Ala Glu Ala Lys Lys
    210                 215                 220

Leu Asn Asp Ala Gln Ala Pro Lys Val Asp Asn Lys Phe Asn Lys Glu
225                 230                 235                 240

Gln Gln Asn Ala Phe Tyr Glu Ile Leu His Leu Pro Asn Leu Asn Glu
                245                 250                 255

Glu Gln Arg Asn Ala Phe Ile Gln Ser Leu Lys Asp Asp Pro Ser Gln
            260                 265                 270

Ser Ala Asn Leu Leu Ala Glu Ala Lys Lys Leu Asn Asp Ala Gln Ala
        275                 280                 285

Pro Lys His His His His His His His Cys
    290                 295


<210> SEQ ID NO 11
<211> LENGTH: 6
<212> TYPE: PRT
<213> ORGANISM: Artificial Sequence
<220> FEATURE:
```

-continued

```
<223> OTHER INFORMATION: Linker sequences

<400> SEQUENCE: 11

Gly Gly Gly Gly Gly Gly
1               5


<210> SEQ ID NO 12
<211> LENGTH: 6
<212> TYPE: PRT
<213> ORGANISM: Artificial Sequence
<220> FEATURE:
<223> OTHER INFORMATION: Linker sequences

<400> SEQUENCE: 12

Gly Ser Gly Ser Gly Ser
1               5


<210> SEQ ID NO 13
<211> LENGTH: 5
<212> TYPE: PRT
<213> ORGANISM: Artificial Sequence
<220> FEATURE:
<223> OTHER INFORMATION: Linker sequences

<400> SEQUENCE: 13

Ser Ser Ser Ser Ser
1               5
```

MULTIVALENT PROTEIN COMPLEXES

CROSS-REFERENCE TO RELATED APPLICATION

This application is a National Stage Application under 35 U.S.C. § 371 and claims the benefit of International Application No. PCT/US2019/033079, filed May 20, 2019, which claims priority to U.S. Application No. 62/674,375, filed May 21, 2018, the disclosure of which is incorporated herein by reference.

TECHNICAL FIELD

This disclosure is related to methods of making and using multivalent protein complexes.

BACKGROUND

Creating a molecule that has multiple binding sites for one or more targets is usually difficult. One approach is to chemically conjugate a number of ligands to a polymer. For examples, polysaccharides, poly(ethylene glycol) (PEG), N-(2-hydroxypropyl)methacrylamide (HPMA) or synthetic dendritic polymers are often used for chemical conjugation of binding proteins. However, making such conjugated molecules typically has a high cost and low yield, and it is difficult to manufacture in a large scale. Another approach is to covalently crosslink the binding ligands with a reactive crosslinker, for example, crosslinking proteins with glutaraldehyde. This kind of crosslinking typically creates randomly oriented and clustered protein complexes, which often have a compromised function.

As multivalent protein complexes have various applications, there is a need to develop a more efficient method of creating a multivalent protein complex.

SUMMARY

This disclosure is related to methods of making and using multivalent protein complexes.

The disclosure provides a composition comprising a multi-protein complex comprising a polypeptide comprising two or more Fc-binding domains, and two or more Fc-containing proteins, each comprising an Fc region, wherein each Fc-containing protein binds to the Fc-binding domain in the polypeptide.

In some embodiments, the Fc-containing proteins are antibodies, heavy-chain antibodies, bispecific antibodies, or Fc-fusion proteins.

In some embodiments, the multi-protein complex can bind to two or more target molecules in a solution or on a solid surface.

In some embodiments, the Fc-binding domains are IgG-binding domains of Staphylococcal Protein A or any functional variants thereof, IgG-binding domains of Streptococcal Protein G or any functional variants thereof, or the Fc-binding domains of natural or engineered Fc-binding proteins.

In some embodiments, the two or more Fc-binding domains in the polypeptide are connected by a linker sequence.

In some embodiments, the Fc-binding domain has a sequence that is at least 90% identical to SEQ ID NO: 1, 2, 3, 4, 5, 6, 7, 8, or 9.

In some embodiments, the Fc-containing protein is an antibody that specifically binds to one or more targets that are selected from the group consisting of CD2, CD3, CD7, CD11a, CD19, CD26, CD27, CD28, CD30, CD30L, CD40, CD43, CD44, CD45RA, CD46, CD49d, CD62L, CD69, CD81, CD95, CD196, CD127, CD137, CD226, BTLA, OX40, ICOS, GITR, PD1, PDL1, CTLA4, HLA-DR, and KLRG-1.

In some embodiments, two or more multi-protein complexes can be further assembled into a super-complex via covalent bonds or non-covalent interactions.

In some embodiments, the two or more Fc-containing proteins in the multi-protein complex are identical.

In some embodiments, the Fc-containing proteins are anti-CD3 antibodies. In some embodiments, the Fc-containing proteins are anti-CD28 antibodies. In some embodiments, the Fc-containing proteins are antibodies that specifically bind to a T cell surface antigen (e.g., CD2, CD27, CD28, CD46 or CD137).

In some embodiments, the composition comprises a plurality of multi-protein complexes comprising two or more different Fc-containing proteins.

In some embodiments, the composition comprises a plurality of multi-protein complexes, each multi-protein complex comprises one or more anti-CD3 antibodies and one or more anti-CD28 antibodies.

Also provided in the present disclosure are methods for modulating a function of a cell. The methods involve contacting the cell with the composition as described herein.

Further, the present disclosure describes methods for activating or expanding T cells. The methods involve contacting the T cells with a multi-protein complex comprising a polypeptide comprising two or more Fc-binding domains, and two or more Fc-containing proteins, each comprising an Fc region, wherein each Fc-containing protein binds to the Fc-binding domain in the polypeptide.

In some embodiments, the multi-protein complex comprises an anti-CD3 antibody and an anti-CD28 antibody.

In some embodiments, the complex further comprises an anti-CD2 antibody, an anti-CD27 antibody, an anti-CD28 antibody, an anti-CD46 antibody or an anti-CD137 antibody, or a combination thereof.

Additionally, described herein are methods for activating or expanding T cells. The method involve contacting the T cells with a first multi-protein complex comprising a first polypeptide comprising two or more Fc-binding domains, and two or more anti-CD3 antibodies, wherein the anti-CD3 antibodies bind to the Fc-binding domain in the first polypeptide, and a second multi-protein complex comprising a second polypeptide comprising two or more Fc-binding domains, and two or more anti-CD28 antibodies, wherein the anti-CD28 antibodies bind to the Fc-binding domain in the second polypeptide.

In some embodiments, the method further comprising contacting the T cells with a third multi-protein complex comprising a third polypeptide comprising two or more Fc-binding domains, and two or more Fc-containing proteins, each comprising an Fc region, wherein each Fc-containing protein binds to the Fc-binding domain in the third polypeptide, wherein the Fc-containing proteins are anti-CD2 antibodies, anti-CD27 antibodies, anti-CD28 antibodies, anti-CD46 antibodies or anti-CD137 antibodies.

In some embodiments, the cell is CD8+ cell or the cells are CD8+ cells.

The disclosure also provides a kit comprising the composition as described herein. In some embodiments, the kit comprises a first vessel containing a composition comprising a polypeptide comprising two or more Fc-binding domains, and a second vessel containing a composition comprising a first Fc-containing protein.

In some embodiments, the kit further comprises a third vessel containing a composition comprising a second Fc-containing protein.

The present disclosure also provides a multi-protein complex comprising a protein comprising two or more Fc-binding domains and two or more Fc-containing proteins (e.g., antibodies or Fc-fusion proteins). In some embodiments, the Fc-containing proteins are tightly bound to the Fc-binding domains. The complex can be stable and soluble in common buffers and cell culture media, providing a useful tool for crosslinking molecules in a solution, on cell-surface, or on a solid surface.

For example, the complex can interact with multiple targets simultaneously. Accordingly, the complex is a multivalent binding agent for one or more antigens/target molecules that the antibodies/Fc-fusion proteins can recognize, resulting an improved binding affinity between the complex and the targets.

In some embodiments, the complex has high degree of flexibility due to the inherent flexibility of the Fc-binding protein. The linker regions between the Fc-binding domains in of the Fc-binding protein can provide a high degree of freedom for the Fc-binding domains, delivering the freedom of movement to the bound Fc-containing proteins. The flexibility of the complex can be important for its capability of adapting to the shape or terrain of cell surface, providing greater efficiency for recognizing and capturing the cell surface targets.

In some embodiments, the complex is soluble in buffers and/or media (e.g., cell culture media). In some embodiments, the complex is not sticky to (e.g., does not bind to) surfaces of plastic, glass or metal containers (e.g., under the cell culture conditions).

In some embodiments, the complex can interact and crosslink multiple copies of a target. The target can be e.g., on a surface (e.g., cell surface) or in a solution.

In some embodiments, the complex can be used to crosslink two targets or two cells when the complex contains two different antibodies/Fc-fusion proteins which recognize the specific cell surface molecules on the two cells, respectively.

In some embodiments, the complex can be used to modulate functions of cells, e.g., inducing or inhibiting certain functions of a population of cells in vitro, ex vivo, or in vivo by crosslinking a number of cell surface molecules.

In some embodiments, the complex can be used in T cell activation and expansion in vitro or ex vivo.

In one aspect, the disclosure provides a complex comprising a primary signal (e.g. anti-CD3 antibody) for T cell activation and expansion.

In one aspect, the disclosure provides a complex comprising a costimulatory signal (e.g., anti-CD28 antibody) for T cell activation and expansion.

In some embodiments, the complex comprises both a primary signal and a costimulatory signal for T cell activation and expansion.

In some embodiments, more than one complexes comprising a primary and a costimulatory signal are used in T cell activation and expansion.

In some embodiments, the complexes can comprise antibodies against T cell surface antigens including, e.g., CD2, CD27, CD46, CD137, and/or CD226.

In some embodiments, the complex can lead to efficient expansion of T cells, resulting 2 to 100,000-fold of expansion in vitro or ex vivo.

In some embodiments, the expanded T cells can include, e.g., $CD4^+$ or $CD8^+$ T cells.

In some embodiments, the complex can be used in NK cell activation and proliferation in vitro or ex vivo.

In some embodiments, the complex can be used for killing malignant cells including cancer cells (e.g., in vitro or in vivo).

In addition, the disclosure provides multi-protein complexes comprising an Fc-binding protein and at least two Fc-containing proteins. The complexes have the capability of binding and crosslinking two or more targets in a solution or on a solid surface, wherein the Fc-binding protein is stably associated with the Fc-containing proteins, wherein the Fc-binding protein comprises at least two Fc-binding domains.

In some embodiments, the Fc-binding domains are selected from the group of the immunoglobulin-binding domains of Staphylococcal Protein A or any functional variants thereof, IgG-binding domains of Streptococcal Protein G or any functional variants thereof, and natural or engineered Fc-binding proteins/peptides. The Fc-binding domains can be connected with or without a linker region.

In some embodiments, two or more molecules of the same Fc-containing proteins are bound to one Fc-binding protein to form a monospecific complex.

In some embodiments, two or more different Fc-containing proteins are bound to one Fc-binding protein to form a dual-/multi-specific complex.

In some embodiments, two or more complexes can be further assembled into a super-complex via covalent or non-covalent interactions among the Fc-binding proteins.

In some embodiments, the Fc-binding protein can comprise additional tags, fragments, domains or modifications in its sequence.

In some embodiments, the Fc-containing proteins include antibodies and/or Fc-fusion proteins, wherein said antibody is an immunoglobulin molecule (e.g., having two heavy chains and two light chains), a heavy-chain antibody, a bispecific antibody, a monoclonal antibody, a polyclonal antibody, or a labeled or modified antibody, and wherein the Fc-fusion protein is an engineered chimeric protein containing at least one Fc region in its sequence.

In some embodiments, the Fc-containing proteins are anti-CD2, anti-CD3, anti-CD7, anti-CD11a, anti-CD19, anti-CD26, anti-CD27, anti-CD28, anti-CD30, CD30L, anti-CD40, anti-CD43, anti-CD44, CD45RA, anti-CD46, anti-CD49d, anti-CD62L, anti-CD69, anti-CD81, anti-CD95, CD196, anti-CD127, anti-CD137, anti-CD226, anti-BTLA, anti-OX40, anti-ICOS, anti-GITR, anti-PD1, anti-PDL1, anti-CTLA4, anti-HLA-DR, anti-KLRG-1 antibodies, or the combinations thereof.

In some embodiments, the monospecific complex comprises an anti-CD3 antibody.

In some embodiments, the monospecific complex comprises an anti-CD28 antibody.

In some embodiments, the monospecific complex further comprises an antibody against T cell surface proteins including, e.g., CD2, CD27, CD28, CD46 or CD137.

In some embodiments, the dual-specific complex comprises both anti-CD3 and anti-CD28 antibodies.

In some embodiments, the complex has the capability of activating and/or expanding T cells in vitro, ex vivo or in vivo.

In some embodiments, the complex has the capability of targeting multiple cell surface molecules simultaneously and/or having the capability of inducing or inhibiting a cellular function.

Further, the present disclosure describes kits comprising an Fc-binding protein and at least one Fc-containing protein, wherein the Fc-binding protein and the Fc-containing protein are supplied separately, and wherein the Fc-binding protein and the Fc-containing protein can be mixed at molar ratio to form a complex. In some embodiments, each complex is pre-formed.

Also provided in the present disclosure are methods for inducing or inhibiting a function of a cell, comprising contacting the cell with a plurality of complexes.

Additionally, described herein are methods of activating and expanding T cells by contacting the T cells with a plurality of the complexes as described herein, wherein the complexes comprises an anti-CD3 antibody for activating TCR/CD3 signaling pathway and an anti-CD28 antibody as a costimulatory signal.

In some embodiments, the complex further comprises a costimulatory antibody against CD2, CD27, CD28, CD46 or CD137.

As used herein, the term "protein" refers to a macromolecule having one or more long chains of amino acid residues. A protein can have one or more polypeptide chains (e.g., 1, 2, 3, 4, 5, 6 or more polypeptide chains). The amino acids in the protein can be modified by some other molecules, e.g., saccharides and/or lipids.

As used herein, the terms "multi-protein complex", "protein complex" and "complex" are used interchangeably and refer to a quaternary protein structure having two or more polypeptide chains. The polypeptide chains within the protein complex can be associated with each other by non-covalent interactions or covalent linkages (e.g. disulfide bond).

As used herein, the term "super-complex" refers to a stable association of two or more multi-protein complexes.

As used herein, the term "domain" refers to a protein unit which has a distinct structure and/or function. A protein domain typically has a recognizable tertiary structure and can exist independently of the rest of the protein.

As used herein, the term "multi-domain" refers to two or more domains in a protein.

As used herein, the term "Fc" or "Fc-region" refers to the "fragment crystallizable" region of an immunoglobulin molecule, or variants thereof.

As used herein, the term "Fc-binding protein" refers to a protein that can bind to the Fc-region. The Fc-binding protein can have one, two, three, four, or more polypeptides.

As used herein, the term "Fc-binding polypeptide" refers to an engineered or natural occurring polypeptide that can bind to the Fc-region. An Fc-binding polypeptide is also an Fc-binding protein.

As used herein, the term "Fc-binding domain" refers to a protein domain that can bind to the Fc-region.

As used herein, the term "Fc-fusion protein" refers to an engineered chimeric protein which has an Fc-region and a non-Fc region.

As used herein, the term "Fc-containing protein" refer to a protein molecule having an Fc-region. The Fc-containing proteins can include, without limitation, antibodies, heavy-chain antibodies, variants of antibodies, and Fc-fusion proteins.

As used herein, the term "multivalent" refers to having more than one binding sites for antigens or targets.

As used herein, the term "avidity" refers to an enhanced binding strength between two molecules due to multiple affinities.

As used herein, the term "crosslink" refers to a direct or indirect connection that links one molecule or target to another. A crosslink can be made by a covalent bonding or a non-covalent interaction. In some embodiments, a crosslink is mediated by a crosslinker which is an intermediate molecule or complex that interacts with both targets.

As used herein, the terms "antigen" and "target" are used interchangeably and refer to a molecule that is recognized specifically by an antibody or variants thereof. In some embodiments, the target is a receptor.

As used herein, the term "Protein A" refers to a 42 kDa surface protein encoded by the gene spa in *Staphylococcus aureus*. The Ig-binding domains of Protein A are Fc-binding domains, which have high affinity to the Fc-region of immunoglobulin G.

As used herein, the terms "domain Z" and "Z domain" are used interchangeably herein to refer a modified version of the domain B of Protein A. The "Z domain" (SEQ ID NO: 6) comprises a mutation at Gly29 residue of the domain B of Protein A.

As used herein, the term "Protein G" refers to the immunoglobulin and albumin binding protein encoded by the gene spg in group C and G Streptococcal bacteria.

As used herein, the term "linker region" or "linker sequence" refers to a segment of amino acids that connect two protein domains. A linker can be an intermediate domain, a loop region or a disordered region.

As used herein, the term "affinity tag" refers to a segment of amino acid sequence which has specific affinity to another molecule or target. Examples of affinity tags include, e.g., poly-Histag, Strep-tag, HA-tag, Flag-tag, GST-tag, and Myc-tag, etc.

As used herein, the term "monospecific complex" refers to a complex that has two or more copies of the same Fc-containing proteins (e.g., antibodies or Fc-fusion proteins). The monospecific complex recognizes and binds to a single type antigen/target.

As used herein, the term "dual-specific complex" refers to a complex that has two different Fc-containing proteins (e.g., antibodies or Fc-fusion proteins). The dual-specific complex can recognize and bind to two different targets or two different epitopes on the same target.

As used herein, the term "multi-specific complex" refers to a complex that has two or more different Fc-containing proteins (e.g., antibodies or Fc-fusion proteins). The multi-specific complex can recognize and bind to two or more (e.g., 2, 3, 4, 5, 6, 7, 8, 9, or 10) different targets or epitopes.

As used herein, the term "activation" of T cells refers to activation of a cellular signaling cascade in T cells that ultimately results in cell proliferation, and/or effector function. In some embodiments, the activation of T cells can lead to cell death, depending on the received primary TCR signals and associated costimulatory signals.

As used herein, the term "expansion" of T cells refers to the proliferation of the T cells upon activation.

As used herein, the terms "subject" and "patient" are used interchangeably throughout the specification and describe an animal, human or non-human, to whom treatment according to the methods of the present invention is provided. Veterinary and non-veterinary applications are contemplated by the present invention. Human patients can be adult humans or juvenile humans (e.g., humans below the age of 18 years old). In addition to humans, patients include but are not limited to mice, rats, hamsters, guinea-pigs, rabbits, ferrets, cats, dogs, and primates. Included are, for example, non-human primates (e.g., monkey, chimpanzee, gorilla, and the like), rodents (e.g., rats, mice, gerbils, hamsters, ferrets, rabbits), lagomorphs, swine (e.g., pig, miniature pig), equine, canine, feline, bovine, and other domestic, farm, and zoo animals.

As used herein, the term "about" refers to a deviation of +/−20% of the measured numeric values where applicable. In some embodiments, the derivation is +/−10%, +/−5%, +/−1%, or +/−0.1% of the measured numeric values.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 10 shows the amino acid sequences of five exemplary Ig-binding domains of Protein A (SEQ ID NOS: 1-5), Z domain (SEQ ID NO: 6), Ig-binding domains of Protein G (SEQ ID NOS: 7-9), and an exemplary Fc-binding protein comprising five tandemly connected Z domains (SEQ ID NO: 10).

DETAILED DESCRIPTION

Figure 1A:
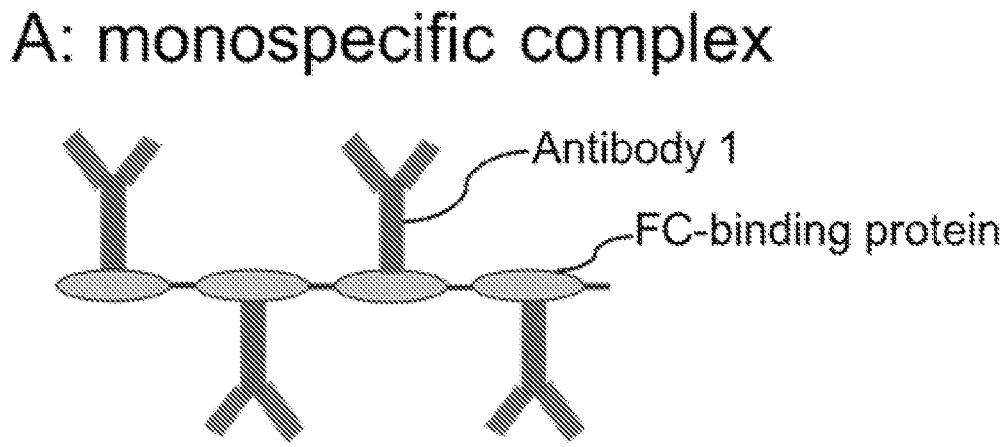
FIG. 1A is diagram showing an example of a monospecific complex. The complex has an Fc-binding protein comprising four Fc-binding domains. Four antibodies are associated with the Fc-binding protein through their Fc regions.

The present disclosure provides methods of creating and using a multivalent protein complex. The protein complex can have multiple binding sites that can bind to or interact with multiple target molecules. Such complex can be very useful in the situations that require simultaneous molecular interactions such as receptor-crosslinking. For example, the complex can facilitate the assembly of CD3-TCR super-complex and expand T cells. Thus, the complex can accelerate the process of Adoptive T-cell Therapy (ACT).

ACT can be used for treating a spectrum of human diseases including cancers owing to its high specificity and effect of long-term immune-protection. In particular, ACT has become a clinical path to a curative cancer therapy for patients with metastatic disease. In clinic settings, the in vitro expansion of T lymphocytes from either peripheral blood mononuclear cells (PBMC), genetically-modified T cells or tumor infiltrating lymphocytes is usually required prior to infusion. The tumor-specific cytotoxic T cells are then infused into cancer patients with the goal of recognizing, targeting, and destroying tumor cells.

T cell activation triggers cellular signaling cascades that can further lead to proliferation, effector function or apoptosis depending on the T-cell receptor (TCR) signal and co-stimulatory signals. It is well established that T cells require at least two independent signals for full activation in vivo (Smith-Garvin et al., "T cell activation." Annual review of immunology 27 (2009): 591-619). In many cases, the primary signal is an antigen-specific signal from binding of an antigenic polypeptide complexed with major histocompatibility complex (MHC) to T cell receptor (TCR). A costimulatory signal is often mediated by cytokines and/or a co-stimulatory signal on antigen-presenting cells (APC). If a costimulatory signal is not provided, T cells activated only by the primary signal will largely result in apoptosis.

Various methods have been developed to activate and expand T cells without involving APC in vitro or ex vivo. Studies showed that the engagement of TCR complex is coupled with the assembly of the CD3 molecules, which form a super-complex with TCR. The crosslinking of the two ε chains of the CD3 leads to the formation of the TCR-CD3 super-complex, which causes a signaling cascade for T cell activation. The antibody against the ε chains of CD3 (e.g. OTK3 clone), when immobilized on a solid surface, can efficiently trigger the TCR-CD3 super-complex formation. Meanwhile, TCR activation is regulated by several co-stimulatory molecules on the T cell surface such as CD28. Therefore, immobilized anti-CD3 and anti-CD28 antibodies are often used for effective T cell activation and expansion in vitro or ex vivo. For example, magnetic beads which are coated with antibodies against CD3 and CD28 is a popular approach to expand T cells ex vivo. Presumably, the surface of antibody-coated microbeads mimics the APC, resulting fast proliferation of T cells. However, the beaded structure bears significant limitations. The rigid surface of the magnetic beads may not be a good substitute for APC. Moreover, completely removing the magnetic beads (i.e., "de-beading") from the T cells in clinic settings can be a challenge. Some other similar methods have been developed. However, these methods usually have various limitations and are difficult to use in a clinical setting as well. For example, a tetrameric complex of CD3 and CD28 was shown to be effective for expanding the T cells. Anti-CD3 and anti-CD28 antibodies anchored on a streptavidin (tetramer) can also activate/expand the T cells. However, those tetramers are not quite effective in activating T cells possibly due to the rigidity of those antibody complexes. Moreover, the high cost of manufacturing those tetramers can make it difficult to be used in large scale T cell expansion. Methods of using the various agents to expand T cells and a general description regarding how to use the T cells in clinical settings are described, e.g., in U.S. Pat. No. 7,572,631B2, US2007/0036783A1 and US patent US2016/0681A; each of which is incorporated herein by reference in its entirety.

The present disclosure provides a method for simple, efficient and versatile formation of a multi-protein complex. When incorporated stimulatory signals for T cell activation, the multi-protein complex can efficiently activate/expand T cell populations (e.g., for expanding T cells that can be used in ACT).

Multi-Protein Complex

The present disclosure provides a multi-protein complex comprising an Fc-binding protein (e.g., an Fc-binding polypeptide) comprising two or more Fc-binding domains, and two or more Fc-containing proteins, each comprising an Fc region, wherein each Fc-containing protein binds to the Fc-binding domain in the polypeptide.

In some embodiments, the multi-protein complex is assembled by at least one Fc-binding protein and two or more Fc-containing proteins.

In some embodiments, the Fc-binding protein or the polypeptide has 2, 3, 4, 5, 6, 7, 8, 9, or 10 Fc-binding domains. The protein complex can have at least two Fc-containing proteins (e.g., 2, 3, 4, 5, 6, 7, 8, 9, or 10 Fc-containing proteins). The Fc-containing proteins can recognize and bind to a specific target. In some embodiments, the protein complex provides more than one (e.g., 2, 3, 4, 5, 6, 7, 8, 9, or 10) binding sites for specific targets.

In some embodiments, the Fc-binding domains in the polypeptide or the Fc-binding protein are fully occupied by the Fc-containing proteins. In some embodiments, the Fc-binding domains in the polypeptide or the Fc-binding protein are not fully occupied by the Fc-containing proteins. For example, 1, 2, 3, 4, 5, 6, 7, 8, 9, or 10 of Fc-binding domains are not occupied by the Fc-containing proteins.

In some embodiments, the protein complex can be used to bind multiple copies of a single type of target. In some other embodiments, the protein complex can be used to bind two or more different targets.

The multi-protein complex can be multivalent. In some embodiments, the complex can be formed by non-covalent interactions between the Fc-binding domains and multiple antibodies/Fc-fusion proteins.

In some embodiments, the multi-protein complex is a monospecific complex. The monospecific complex can be formed with an Fc-binding protein (e.g., a polypeptide) and one type of antibodies/Fc-fusion proteins (FIG. 1A). The antibody can be a monoclonal antibody or a polyclonal antibody which recognizes one target or molecule. The target or molecule can be in a solution or on a surface of a particle (e.g., nanoparticle). A monospecific complex can bind two or more molecules of the same type.

Figure 1B:
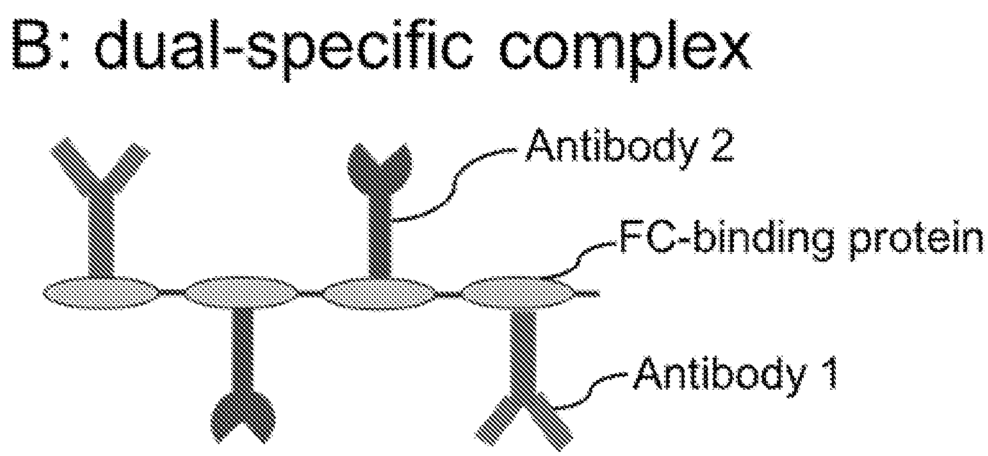
FIG. 1B is a diagram showing an example of dual-specific complex. The complex has two different kind of antibodies (e.g., antibodies specifically bind to different antigens) and a polypeptide comprising four Fc-binding domains.
Figure 4:
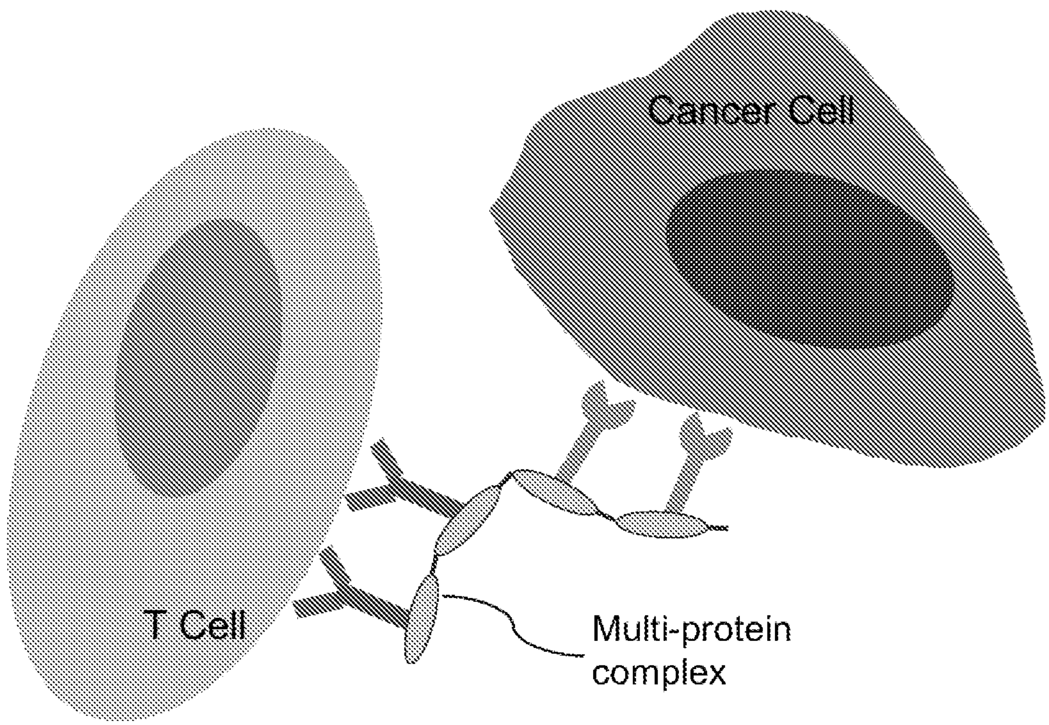
FIG. 4 is a schematic diagram showing the crosslinking of two cells by a multi-protein complex. The dual-specific complex comprises two different antibodies and can bind to two cells and bring them in close proximity.
Figures 5A, 5B, 5C, 5D, 5E, 5F:
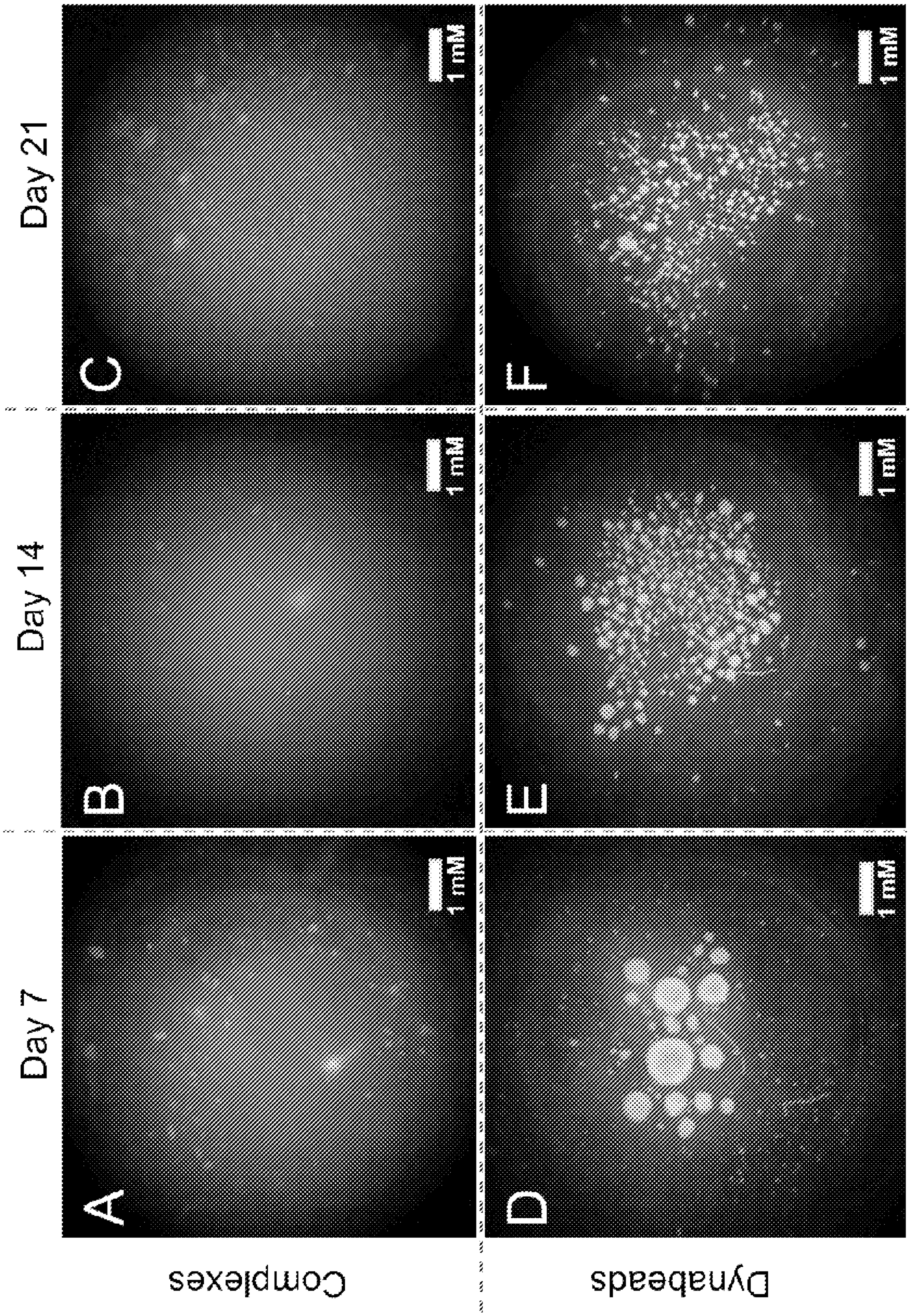
FIGS. 5A-5C are a series of images showing that T cells are expanded by a mixture of monospecific complexes comprising anti-CD3 antibodies and monospecific complexes comprising anti-CD28 antibodies at Day 7, 14, and 21. The T cells expanded by the complexes formed small clusters in a static cell culture condition.
FIGS. 5D-5F are a series of images showing that T cells are expanded by DYNABEADS® (magnetic beads) coated with CD3/CD28 ("Dynabeads"). The T cells expanded by magnetic beads tend to form larger clusters. The results indicate the complex can provide a better contact between the cells and the antibodies than the magnetic beads.

In some embodiments, the multi-protein complex is a dual-specific complex. The dual-specific complex can be formed with an Fc-binding protein and two different antibodies/Fc-fusion proteins (FIG. 1B). The molar ratio of the two antibodies/Fc-fusion proteins bound on the Fc-binding protein can vary (e.g., 1:1, 2:1, 3:1, 4:1, 1:2, 1:3, or 1:4). In some embodiments, equal number of different antibodies/Fc-fusion proteins can bind to a single Fc-binding protein. The dual-specific complex can target two different molecules in a solution or on a surface of a cell or a particle. A dual-specific complex is useful in crosslinking two different targets (e.g., different molecules, different particles, and/or different cells). For example, as shown in FIG. 4, a dual-specific complex can crosslink or bring together a T cell and a cancer cell, wherein in the dual-specific complex binds to a cell surface marker on the T cell and a cell surface marker on the cancer cell at the same time.

In some embodiments, the multi-protein complex is a multi-specific complex. The multi-specific complex can be formed with an Fc-binding protein and two or more than two different antibodies/Fc-fusion proteins. A multi-specific complex can be useful in crosslinking multiple different targets in a solution.

The multi-protein complex exhibits conformational flexibility due to the flexibility of the Fc-binding protein. The inter-domain linkage can be flexible for each Fc-binding domain to have a large degree of freedom. As a result, the complex can better mimic the interaction of an antigen presenting cell with a T cell.

In some embodiments, the multi-protein complex interacts with one type of cell-surface antigen/target when the complex is monospecific. In some other embodiments, a multi-protein complex can interact with more than one cell-surface antigens/targets when the complex is dual- or multi-specific. In some embodiments, the complex can be used to crosslink two or more molecules in a solution or on a solid surface. In some other embodiments, the complex can be used to crosslink two or more cells or particles.

In some embodiments, the complex can be used to modulate cellular functions, e.g., induce or inhibit certain cellular functions by crosslinking the cell surface molecules.

In some embodiments, the complex can be used to activate and expand a population of T cells for treatment of cancers or infectious diseases.

Fc-Binding Protein

The multi-protein complex has a multi-domain Fc-binding protein or Fc-binding polypeptide, which serves as a docking platform for tethering of antibodies and their variants (e.g., full-length antibodies, heavy-chain antibodies), and Fc-fusion proteins. A comprehensive review for the common Fc-binding proteins can be found in the article of "Fc-Binding Ligands of Immunoglobulin G: An Overview of High Affinity Proteins and Peptides" (Choe W. et al. *Materials*. 2016; 9(12): 994), which is incorporated herein by reference in its entirety.

In some embodiments, the Fc-binding protein or the Fc-binding polypeptide comprises at least two (e.g., at least 2, 3, 4, 5, 6, 7, 8, 9, or 10) Fc-binding domains. The Fc-binding domains can be the Ig-binding domains of Staphylococcal Protein A or any functional variants thereof, the Z-domain or any functional variants thereof, the immunoglobulin-binding domains of Streptococcal Protein G or any functional variants thereof, and any other natural or engineered Fc-binding polypeptides. Protein A has five Ig-binding domains, including C (SEQ ID NO: 1), D (SEQ ID NO: 2), E (SEQ ID NO: 3), A (SEQ ID NO; 4) and B (SEQ ID NO: 5). "Z domain" is a modified B domain (as shown in SEQ ID NO: 6). The Ig-binding domains of Protein G from *Streptococcus* sp. group G include C1 (SEQ ID NO: 7), C2 (SEQ ID NO: 8) and C3 (SEQ ID NO: 9). Protein A and Protein G have different affinity to antibodies from different species and/or from different subclasses. Thus, different Fc-binding domains in the Fc-binding protein or Fc-binding polypeptide can be selected based on the antibodies to be used. In some embodiments, the Fc-binding domain is a naturally occurred or engineered Fc-binding polypeptide, e.g., Fc-binding domains of Protein A, Protein G, and Protein L. Examples of the Fc-binding domains or polypeptides can be found in the article "Fc-Binding Ligands of Immunoglobulin G: An Overview of High Affinity Proteins and Peptides" (Choe W. et al. *Materials*. 2016; 9(12): 994), which is incorporated herein by reference in its entirety.

In some embodiments, the Fc-binding protein of the Fc-binding polypeptides comprises or consists of two Fc-binding domains, three Fc-binding domains, four Fc-binding domains, five Fc-binding domains, six Fc-binding domains, seven Fc-binding domains, eight Fc-binding domains, or more than eight Fc-binding domains.

Since the Z domain has limited Fab binding activity, an Fc-binding protein or Fc-binding polypeptide has only Z domains can be used for creating the multi-protein complexes. In some embodiments, the Fc-binding protein or Fc-binding polypeptide has five tandemly connected Z domains (SEQ ID NO: 10), which can accommodate 1, 2, 3, 4, or 5 antibodies in a solution (e.g., about 3-4 antibodies on average in a solution). In some embodiments, the antibodies are anti-CD3 or anti-CD28 antibodies.

In some embodiments, the Fc-binding protein or the Fc-binding polypeptide has a mixture of Fc-binding domains, e.g., C domain, D domain, E domain, A domain, and B domain from Protein A, C1 domain, C2 domain and C3 domain from Protein G, Z domain, some other Fc-binding domains of Fc-binding polypeptides, and variants thereof. Variants of these Fc-binding domains can also be included in the Fc-binding protein or the Fc-binding polypeptide. The variants can have amino acid substitutions, deletions and/or additions and still retain the functional activity of the natural form of the Fc-binding domains as described herein.

In some embodiments, the Fc-binding domains are connected with or without a linker sequence. For example, the five Ig-binding domains in the wild type Protein A are considered to have no inter-domain linker sequences. To increase the flexibility of the Fc-binding protein, an extra inter-domain linker sequence may be added between the neighboring domains. Some examples of linker sequences include GGGGGG (SEQ ID NO: 11), GSGSGS (SEQ ID NO: 12) and SSSSS (SEQ ID NO: 13).

In some embodiments, the Fc-binding domains are connected with a chemical linker, e.g., disulfide, carbodiimide, NHS ester, imidoester, pentafluorophenyl ester, hydroxymethyl phosphine, maleimide, haloacetyl (Bromo- or Iodo-), pyridyldisulfide, thiosulfonate, vinylsulfone, hydrazide, alkoxyamine, diazirine, aryl azide, or isocyanate.

Each Fc-binding domain can have high affinity to the Fc-region of an antibody/Fc-fusion protein. Accordingly, each Fc-binding protein can accommodate two or more copies of an antibody/Fc-fusion protein or two or more molecules of different antibodies/Fc-fusion proteins. In some embodiments, the complex provides a high local ligand density for binding to antigens/targets, resulting in enhanced binding avidity.

In some embodiments, the Fc-binding protein or the Fc-binding polypeptide comprises two or more copies of a single Fc-binding domain (e.g., Z domain).

In some embodiments, the Fc-binding protein or the Fc-binding polypeptide comprises two or more different Fc-binding domains (e.g., B domain and Z domain).

In some embodiments, the Fc-binding polypeptide is engineered to include one or more cysteine residues for further crosslinking of the Fc-binding polypeptide via disulfide bonds.

In some embodiments, the Fc-binding protein or the Fc-binding polypeptide is engineered to include some other functional domains or sequences.

In some embodiments, the Fc-binding protein or the Fc-binding polypeptide include an affinity tag such as, but not limited to, poly-Histag, Strep-tag, HA-tag, Flag-tag, GST-tag, and Myc-tag, etc. The affinity tag, when included, can provide a purification tool for the multi-protein complex. The affinity tag can also provide a method for immobilization of the multi-protein complex on a surface or on another molecule.

In some embodiments, the Fc-binding protein, either a wild type or an engineered variant, can be synthesized in an expression system such as bacteria (e.g. *E. coli*), yeast, algae, insect cells and mammalian cells. After the Fc-binding protein is purified to a homogeneous level, the Fc-binding protein is quantified and reconstituted to a desired concentration in an appropriated buffer.

In some embodiments, the Fc-binding domain can have a sequence that is at least 70%, 80%, 90%, 95%, 96%, 97%, 98%, 99% identical to an immunoglobulin-binding domain described in this disclosure (e.g., domains B, C, A, E, D, Z, C1, C2, and C3).

In some embodiments, the Fc-binding polypeptide can have a sequence that is at least 70%, 80%, 90%, 95%, 96%, 97%, 98%, 99% identical to SEQ ID NO: 10.

Fc-Containing Protein

The Fc-containing proteins are protein molecules having an Fc-region. The Fc-containing proteins can include, e.g., antibodies, heavy-chain antibodies, and Fc-fusion proteins. The Fc fusion protein can be an engineered chimeric protein containing at least one Fc region. The Fc-containing protein, comprising an FC region, can be associated with an Fc-binding protein via the Fc region.

The antibody can be a monoclonal antibody, a polyclonal antibody, or variants thereof. The antibody can also be an immunoglobulin molecule (including two heavy chains and two light chains), or a two-chain heavy-chain antibody.

The Fc-containing proteins can have specific binding affinity to an antigen or a target in a solution or on a solid surface. In some embodiments, the Fc-containing protein is an antibody or Fc-fusion protein that can bind to cell surface markers. In some embodiments, the cell surface markers are tumor cell surface markers.

In some embodiments, the antibodies or the variants thereof are from single animal origin or from multiple animal origins including but not limited to mice, rats, rabbits, horses, sheep, goats, cows, camelids, sharks, pigs, hamsters, humans. In some embodiments, the antibodies are extracted from an animal. In some other embodiments, the antibodies/Fc-fusion proteins are purified from a recombinant protein expression system.

In some embodiments, the Fc-containing protein is an antibody that can recognize T cell surface markers. In some embodiments, the Fc-containing protein provides a primary signal (e.g. anti-CD3) for T cell activation and expansion, and/or a costimulatory signal (e.g. anti-CD28, anti-CD2, anti-CD27, anti-CD46, anti-CD137, anti-CD226) for T cell activation and expansion. In some embodiments, the Fc-containing protein can specifically bind to CD3, CD28, CD2, CD27, CD46, CD137, or CD226.

In some embodiments, the Fc-containing protein is a bispecific antibody. It can provide both a primary signal and costimulatory signal for T cell activation and expansion. In some embodiments, the first arm of the bispecific antibody can bind to CD3, the second arm of the bispecific antibody can bind to CD28, CD2, CD27, CD46, CD137, or CD226.

Methods of Making the Multi-Protein Complex

The complex can be made in many different ways, and complexes with different titrations of Fc-binding proteins and antibodies/Fc-fusion proteins can be formed.

To make a monospecific complex, an antibody/Fc-fusion protein of choice can be mixed with a purified Fc-binding protein at a certain molar ratio. Although more molar quantity of antibody/Fc-fusion protein is used for mixing, the antibody/Fc-binding protein may or may not saturate the binding sites on the Fc-binding protein because of the steric hindrance in the Fc-binding protein. In some embodiments, the molar ratio of the Fc-binding protein to the Fc-containing protein is between about 1:2 and about 1:100 (e.g., between about 1:2 and about 1:10, or between about 1:2 and about 1:5).

To generate a dual-specific or multi-specific complex, equal molar quantity of the two or more antibodies/Fc-fusion proteins can be mixed first. The mixture of the antibodies/Fc-fusion proteins is further mixed with an Fc-binding protein or Fc-binding polypeptide at a desired molar ratio. Alternatively, a desired molar ratio of two or more antibodies/Fc-fusion proteins are mixed. The resultant mixture is further mixed with the Fc-binding protein at a desired molar ratio. In some embodiments, the molar ratio of the two different antibodies/Fc-fusion proteins that are used to form a dual-specific complex can be between about 1:1 and about 1:5 (e.g., about 1:1, 1:2, 1:3, 1:4, or 1:5). In some embodiments, the various antibodies/Fc-fusion proteins that are used to form a multi-specific complex is about equal molar.

The interaction of the components that are mixed together can be very quick. Therefore, the complex can be formed within a short period (e.g. less than 6 hours, 1 hour, 10 minutes or 1 minute).

The complex can be further purified with a chromatographic method. The purification of the complex can be based on the affinity tag that the Fc-binding protein has. For separation of various populations of the complexes in a solution, ionic exchange chromatography can be used. The ionic exchange chromatography can separate different populations of the complexes based on the differential charges that various antibodies/Fc-fusion proteins have in the complexes.

In some embodiments, the complex is stable and soluble in a range of temperature, e.g., 0-40° C., preferably 4-37° C.

In some embodiments, two or more complexes are mixed together to form a composition.

In some embodiments, two more complexes are mixed together and are further crosslinked with a disulfide bond or other chemical linkers.

In some embodiments, a multi-protein complex, after being generated, can be further purified with a liquid chromatographic method such as, not limited to, size exclusion/gel filtration, affinity chromatography, ionic exchange chromatography and hydrophobic chromatography. The purified complex in a solution can be concentrated or diluted to a desired concentration. In some embodiments, the complex in a solution can be stored for a prolonged period at various conditions such as at different temperature conditions.

The disclosure further provides a vector comprising a sequence that encodes an amino acid sequence as described herein, and cells comprising these vectors. The present disclosure also provides recombinant vectors (e.g., an expression vectors) that include a nucleic acid as disclosed herein (e.g., a nucleic acid that encodes a polypeptide disclosed herein), host cells into which are introduced the recombinant vectors (i.e., such that the host cells contain the polynucleotide and/or a vector comprising the polynucleotide), and the production of polypeptides or proteins thereof by recombinant techniques.

The disclosure also provides a nucleic acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any nucleotide sequence as described herein, and an amino acid sequence that is at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% identical to any amino acid sequence as described herein. In some embodiments, the disclosure relates to nucleotide sequences encoding any polypeptides that are described herein, or any amino acid sequences that are encoded by any nucleotide sequences as described herein. In some embodiments, the nucleic acid sequence is less than 10, 20, 30, 40, 50, 60, 70, 80, 90, 100, 110, 120, 130, 150, 200, 250, 300, 350, 400, or 500 nucleotides. In some embodiments, the amino acid sequence is less than 5, 6, 7, 8, 9, 10, 20, 30, 40, 50, 60, 70, 80, 90, 100, 110, 120, 130, or 150 amino acid residues.

In some embodiments, the amino acid sequence (i) comprises an amino acid sequence; or (ii) consists of an amino acid sequence, wherein the amino acid sequence is any one of the sequences as described herein. In some embodiments, the nucleic acid sequence (i) comprises a nucleic acid sequence; or (ii) consists of a nucleic acid sequence, wherein the nucleic acid sequence is any one of the sequences as described herein.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The length of a reference sequence aligned for comparison purposes is at least 80% of the length of the reference sequence, and in some embodiments is at least 90%, 95%, or 100%. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences. For purposes of the present invention, the comparison of sequences and determination of percent identity between two sequences can be accomplished using a Blossum 62 scoring matrix with a gap penalty of 12, a gap extend penalty of 4, and a frameshift gap penalty of 5.

Methods of Using the Complex

The multi-protein complex can be used to bind a plurality of cell surface proteins to modulate a cellular function, for example, inducing or inhibiting a cellular function.

In some embodiments, the complex can bind to a population of T cells, providing a primary and a costimulatory signal to the T cells. In some embodiments, the complex can be used to activate and/or expand T cells.

The starting T cells can be obtained from peripheral blood mononuclear cells (PBMC) of blood of donors of a subject (e.g., a human). T cells can also be obtained from a number of other sources including bone marrow, lymph node tissue, cord blood, thymus tissue, tissue from a site of infection, ascites, pleural effusion, spleen tissue, and tumors. In some embodiments, any T cell lines that are known in the art can be used. The T cells used in this experiment can be isolated by depleting B cells, NK cells, monocytes, platelets, dendritic cells, granulocytes and erythrocytes. The techniques of T cell isolation are known to an ordinarily skilled person in the field.

Figure 3:
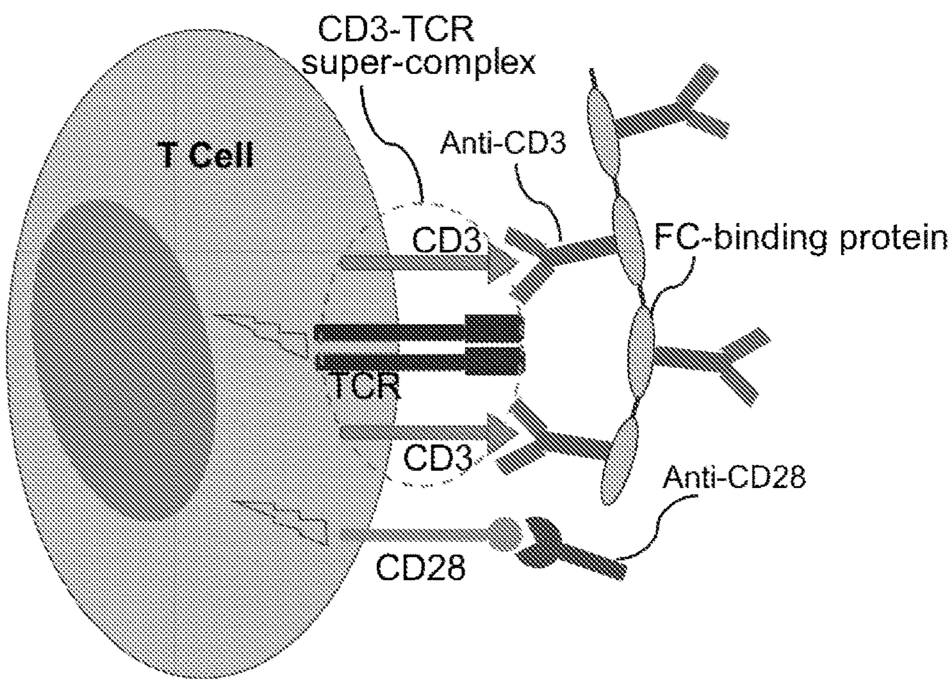
FIG. 3 is a schematic diagram showing the crosslinking of CD3 by a monospecific complex comprising anti-CD3 antibodies. Crosslinking of CD3 ε chains leads to the assembly of CD3-TCR super-complex. With a costimulatory signal (e.g. anti-CD28 antibodies), the T cell can be activated and starts to proliferate.

In some embodiments, the monospecific complex comprising two or more copies of anti-CD3 antibody is supplied as the primary signal for T cell activation and proliferation. The monospecific anti-CD3 complex crosslinks the s chains of CD3 and triggers the assembly of the CD3-TCR supercomplex on the T cells (FIG. 3). The assembled CD3-TCR transduces a singling cascade leading to the activation of the T cells.

In some embodiments, a monospecific complex comprising two or more copies of anti-CD28 antibody can provide the costimulatory signal for T cell activation.

In some embodiments, a monospecific complex comprising two or more copies of an antibody selected from the group of, without limitation, anti-CD2, anti-CD7, anti-CD27, anti-CD46, anti-CD137 and anti-CD226 can be used as another costimulatory signal.

In some embodiments, complexes comprising a primary signal and a stimulatory signal, are used to treat the T cells. For example, a monospecific anti-CD3 complex and a monospecific anti-CD28 complex can be used together for efficient T cell activation and expansion.

Figure 2:
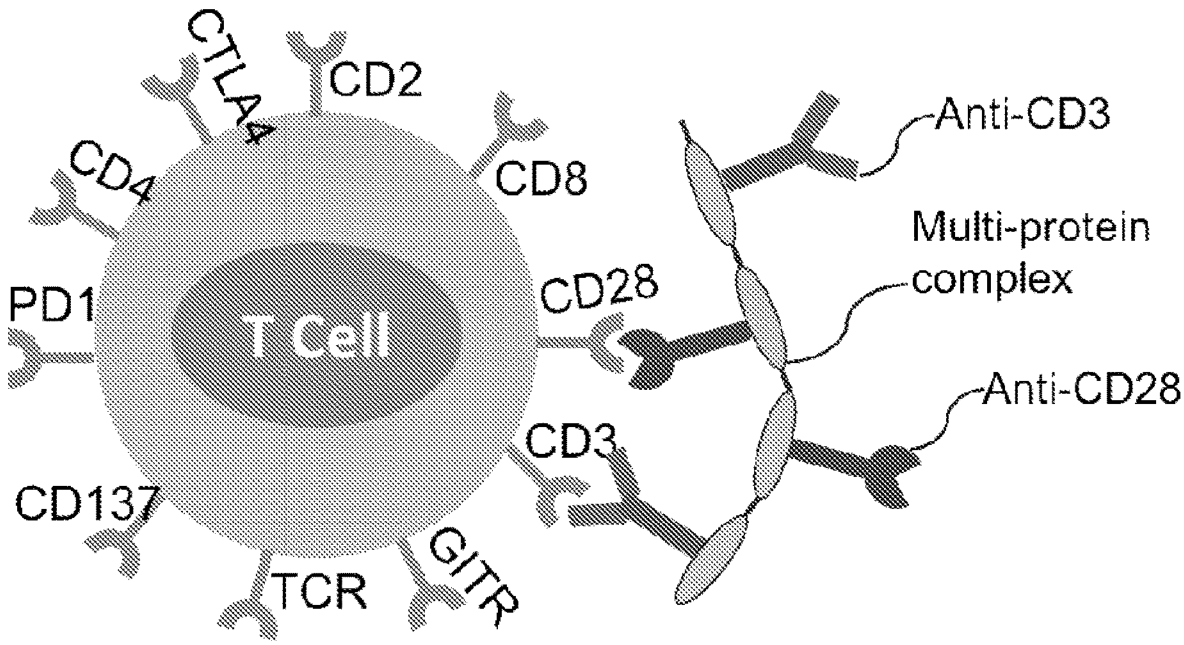
FIG. 2 is a schematic diagram showing the interaction between a dual-specific complex and T cell surface markers on a T cell. The complex comprises anti-CD3 antibodies (a primary signal for T cell activation) and anti-CD28 antibodies (a costimulatory signal for T cell activation). The complex can change its conformation and bind to the T cell surface makers on the T cell surface more efficiently.

In some embodiments, the molar ratio of the different monospecific complexes used for treating T cells is adjustable. For example, the molar ratio of a complex having the primary signal (e.g. anti-CD3) and a complex having the costimulatory signal (e.g. anti-CD28) can be between about 1:1 and about 1:100. The molar ratio of a complex having the primary signal (e.g. anti-CD3) and a complex having the costimulatory signal (e.g. anti-CD28) can also be between about 1:100 and about 1:1 (FIG. 2).

The ratio as described herein (e.g., primary signal:costimulatory signal, or costimulatory signal:primary signal) can be greater than 1:100, 1:90, 1:80, 1:70, 1:60, 1:50, 1:40, 1:30, 1:20, 1:10, 1:5, 1:2, or 1:1. The ratio can also be less than 1:100, 1:90, 1:80, 1:70, 1:60, 1:50, 1:40, 1:30, 1:20, 1:10, 1:5, 1:2, or 1:1.

In some embodiments, an un-complexed antibody which provides a costimulatory signal and a monospecific complex comprising an anti-CD3 antibody are used together for T cell activation (FIG. 3). In some embodiments, an anti-CD28 antibody and a monospecific complex comprising anti-CD3 are used together for T cell activation. In some other embodiments, two or more un-complexed costimulatory antibodies and a monospecific complex comprising anti-CD3 are used for T cell activation. The term "un-complexed" as used herein refers to a soluble antibody which is not associated with an Fc-binding protein.

In some embodiments, additional costimulatory signals include antibodies selected from the group of, without limitation, anti-CD2, anti-CD7, anti-CD27, anti-CD46, anti-CD137 and anti-CD226. These antibodies can be in a complex or un-complexed, and be added to the monospecific complexes of anti-CD3 and anti-CD28 for T cell activation.

In some embodiments, a dual-specific complex, comprising both an anti-CD3 and an anti-CD28 antibody, are used for T cell activation (FIG. 2).

In some embodiments, a dual-specific complex, comprising both an anti-CD3 and an antibody for costimulatory signal selected from the group of, without limitation, anti-CD2, anti-CD7, anti-CD27, anti-CD46, anti-CD137 and anti-CD226, can be used for T cell activation.

In some embodiments, additional costimulatory signals comprising complexed and/or un-complexed antibodies selected from the group of, without limitation, anti-CD2, anti-CD7, anti-CD27, anti-CD46, anti-CD137 and anti-CD226, can be added to the dual-specific complex of anti-CD3 and anti-CD28 for T cell activation.

In some embodiments, different pre-assembled complexes and any un-complexed antibodies are added to the T cell culture medium individually. In some other embodiments, different pre-assembled complexes and any un-complexed antibodies are pre-mixed before adding to the T cell culture medium.

In some embodiments, the cell culture container is blocked by a non-toxic hydrophilic material to prevent the potential immobilization of the multi-protein complexes. At least, a portion of complexes are kept in soluble state in the cell culture medium.

In some embodiments, based on calculation of the molarity of the complexes, each T cell to be activated is covered by at least one complex comprising anti-CD3 and one complex comprising anti-CD28. Additional complexes comprising anti-CD3 and/or anti-CD28 can be added during the expansion course of the T cells.

In some embodiments, the excessive complexes comprising anti-CD3 and/or anti-CD28 are removed by an affinity resin which specifically binds the complexes (e.g., affinity tags in the complexes).

In some embodiments, the T cells activated by the complexes as described herein can expand about 2-100000 folds (e.g., more than 2, 3, 4, 5, 6, 7, 8, 9, 10, 20, 30, 40, 50, 60, 70, 80, 90, 100, 500, 1000, 5000, 10000, 50000, or 100000 folds) in 2-30 days (e.g., 2, 3, 4, 5, 6, 7, 8, 9, 10, 20, or 30 days). In some embodiments, the T cells can be expanded by over 10-fold, 100-fold, 1000-fold, 2000-fold, 4000-fold, 100,000-fold or more during an appropriate period (e.g., 21 days) by using the multi-protein complexes disclosed herein.

In some embodiments, the complexes are very efficient for T cell expansion in vitro and ex vivo. In some embodiments, the T cell expansion efficiency by the methods described herein is about 2-20 times higher than the magnetic beads-based expansion.

In some embodiments, the T cells expanded by the complexes have equal or less terminally expanded cells or apoptotic cells than beads-based expansion.

In some embodiments, the T cells expanded by the complexes as described herein have over 90%, 91%, 92%, 93%, 94%, 95%, 96%, 97%, 98%, 99%, 99.1%, 99.2%, 99.3%, 99.4%, or 99.5% of cell viability (e.g., 1, 2, 3, 4, 5, 6, 7, 8, 9, 10, 11, 12, 13, 14, 15, 16, 17, 18, 19, 20, 21, 22, 23, 24, or 25 days after the expansion starts).

In some embodiments, the T cells expanded by the complexes express antigens of CD4 and CD8 at a ratio between 1:1 and 1:20 (e.g., 1:2, 1:3, 1:4, 1:5, 1:10, 1:15, or 1:20). In some embodiments, the complexes and methods as described herein can induce an expanded T cell population having a greater proportion of CD8+ cells than beads-based expansion. In some embodiments, the proportion of CD8+ cells among T cells (e.g., CD8+ cells and CD4+ cells) is greater than 10%, 20%, 30%, 40%, 50%, 60%, 70%, 80%, 90%, or 95%. In some embodiments, the proportion of CD4+ cells among T cells (e.g., CD8+ cells and CD4+ cells) is lower than 5%, 10%, 20%, 30%, 40%, 50%, 60%, 70%, 80%, or 90%. In some embodiments, the complex as described herein can increase the percentage of CD8+ cells by more than 10%, 15%, 20%, 25%, 30%, 35%, 40%, 45%, 50%, 55%, 60%, 65%, 70%, 75%, 80%, 85%, 90%, or 95%. In some embodiments, the complex as described herein can decrease the percentage of CD4+ cells in T cells by more than 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, or 95%.

In some embodiments, the T cells are collected from a subject, and are expanded by the methods described herein. The expanded T cells can be used for various purposes, e.g., adoptive cell transfer.

In some embodiments, a dual-specific complex comprising two different antibodies/Fc-fusion proteins can be used to crosslink two different cells by binding one cell with one antibody/Fc-fusion protein on the complex and binding the other cell with the other antibody/Fc-fusion protein on the complex.

In some embodiments, the T cells are expanded in the presence of IL-2.

In some embodiments, a dual-specific complex comprising an antibody recognizing an antigen on a T cell and comprising another antibody recognizing a tumor cell surface marker can crosslink the T cell and the tumor cell (FIG. 4). In some embodiments, the crosslink can kill the tumor cells.

Thus, the disclosure also provides a method of killing cancer cell. The methods can involve contacting the cancer cell with a multi-protein complex as described herein. In some embodiments, the multi-protein complex can recognize and bind to a specific cell surface molecule on an immune cell (e.g., CD2, CD27, CD46, CD137, and/or CD226), and a specific cell surface molecule on a cancer cell (e.g., PD-L1, Her2, and CD20). Therefore, the present disclosure also provides a method of treating cancer in subject.

In some embodiments, the complex can be used for capturing and isolating a specific type of cells. The complex can comprise an antibody/Fc-fusion protein that recognizes a specific surface protein on the cells to be captured. In some embodiments, the Fc-binding protein can have an affinity tag including, e.g., poly-His tag and Strep-tag. Once the cells are bound by a number of the complex, a matrix comprising solid particles or membrane and a binding moiety that specifically interacts with the affinity tag on the Fc-binding protein within the complex can be used to pull-down the cells.

Compositions and Kits

The present disclosure also provides a composition or a pharmaceutical composition comprising the complex.

In some embodiments, the compositions are formulated with a pharmaceutically acceptable carrier. The pharmaceutical compositions and formulations can be used in vitro, in vivo, or ex vivo, or can be administered parenterally, topically, orally or by local administration.

In some embodiments, the complex is stable in a buffer (e.g. Phosphate buffer, Bicarbinate buffer) or a medium (e.g. DMEM, X-VIVO-15), due to the high affinity interaction between the Fc-binding protein and the antibody/Fc-fusion protein. The complex can maintain its structure in a wide range of conditions, such as various temperatures (e.g. 0° C. to 37° C.), various pH (e.g. pH 5 to pH 9), various ionic strengths (e.g. 0-2,000 ms/cm), and/or in the presence of a detergent (e.g. TWEEN-20).

In some embodiments, the complex can be completely soluble in a solution, a buffer or a medium over a wide range of temperatures (e.g. 4° C. to 37° C.) and pH (e.g. pH 5 to pH 9).

The present disclosure further provides T cell expanding kits comprising the multi-protein complexes, antibodies, other components, and instructions of using thereof.

EXAMPLES

The invention is further described in the following examples, which do not limit the scope of the invention described in the claims.

Example 1: Materials and Methods

The following materials and methods were used in the examples.

Source of T Cells

Prior to expansion, the starting T cells were obtained from peripheral blood mononuclear cells (PBMC) of human blood of donors. The T cells used in the examples were isolated by depleting B cells, NK cells, monocytes, platelets, dendritic cells, granulocytes and erythrocytes.

T Cell Culture

A 48-well cell culture plate was first blocked with a phosphate buffered saline (PBS) with 2.0% human serum albumin (HSA) for 18 hours at 37° C. Blocking with HSA prevented the multi-protein complexes from being immobilized on the plastic surface. The excessive HSA was washed out by PBS. The isolated T cells from PBMC were cultured in the X-VIVO™ 15 (Lonza, Basel, Switzerland) with 5% human AB serum and 10-20 IU/mL of IL-2 starting at the cell density of 0.1-1.0×$10^6$/mL. All the cells were cultured in a 37° C. incubator with 5% $CO_2$ and 75% humidity.

Antibodies

Mouse anti-human CD3 ("OKT3") and mouse anti-human CD28 ("CD28.2") monoclonal antibodies were purchased from Life Technologies (Carlsbad, CA). Both antibody solutions were diluted to 0.2 μg/μL.

Fc-Binding Protein

A polypeptide containing five Z domains (SEQ ID NO: 10) was designed and expressed in a yeast system. The secreted protein was purified with a Superdex S75 gel filtration chromatographic column (GE Healthcare, Boston, MA). The purified protein was reconstituted to a concentration of 0.2 μg/μL in PBS.

Dynabeads

Dynabeads ClinExVivo™ CD3/CD28 (or "Dynabeads", from Thermo Fisher Scientific, Waltham, MA), was used for comparison purpose. A bead to cell ratio of 3:1 was used in the experiments.

Tetrameric Antibody Complex (TAC)

A T cell activator, "ImmunoCult™ Human CD3/CD28 T Cell Activator" (from STEMCELL Technologies, Vancouver, Canada) was also used for comparison purpose. About 25 μL of TAC solution was added to 1 mL of culture solution for T cell expansion.

Streptamer CD3 CD28 Premix

A T cell activator, Streptamer CD3/CD28 Premix solution (from IBA Lifesciences, Gottingen, Germany) was also used for T cell expansion.

Example 2: Formation of the Multi-Protein Complexes

Figure 9:
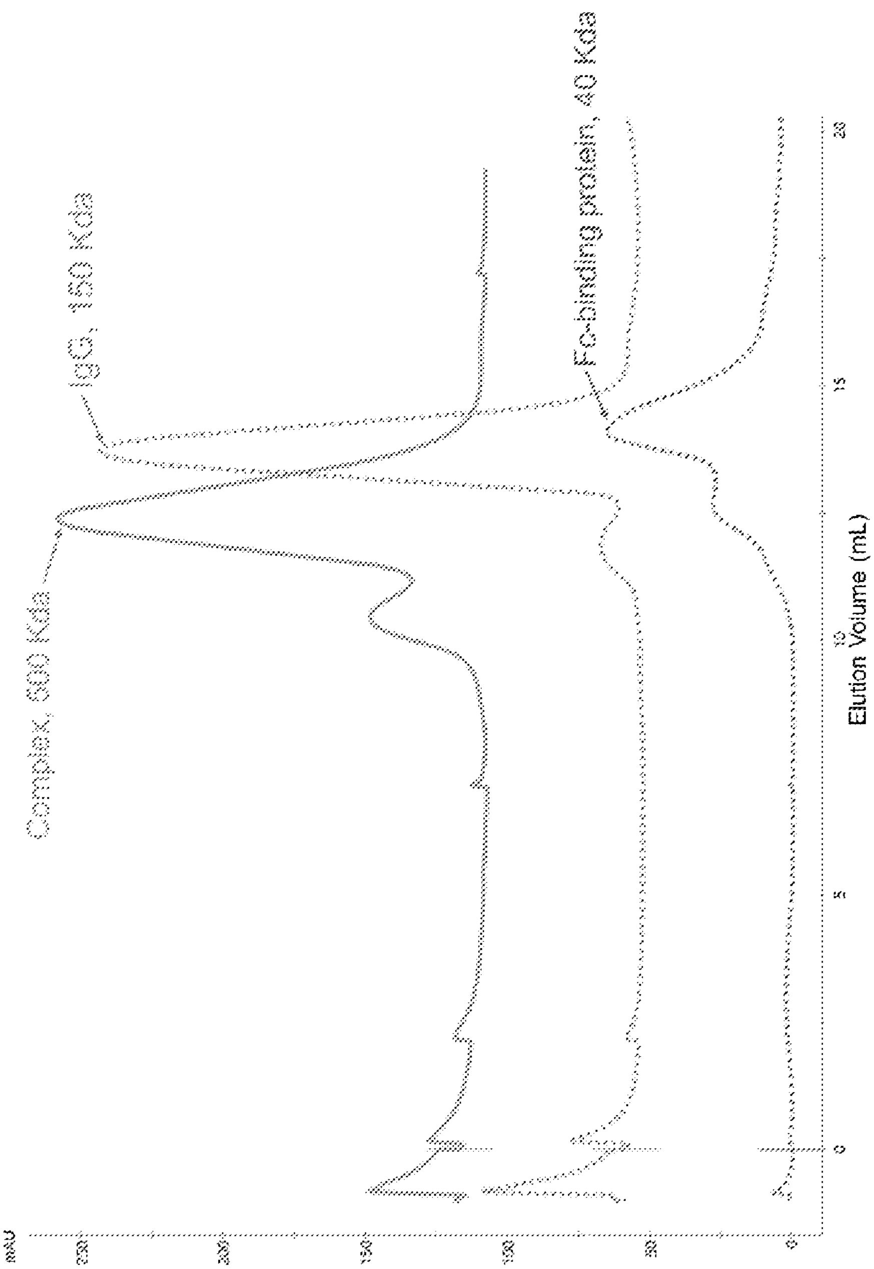
FIG. 9 shows the formation and purification of a complex of an Fc-binding protein and a human IgG antibody. The Fc-binding protein (SEQ. ID NO: 10), the IgG antibody, and the complex were subjected to a gel filtration column (GE Healthcare Superdex S200). The complex was formed by mixing the Fc-binding protein and the IgG antibody at a molar ratio of about 1:3 (as described in Example 2). The elution chromatograms were overlaid to show the difference of the elution volumes which indicate the molecular weight of the three proteins and the stoichiometry of the complex.

Experiments were performed to make monospecific complexes of anti-CD3 antibodies and anti-CD28 antibodies. To confirm the formation of the complex between an Fc-binding protein and a human IgG antibody and to estimate the stoichiometry of the complex, the complex, the Fc-binding protein, and the human IgG were subjected to a gel filtration chromatography (GE Healthcare Superdex 5200), respectively (FIG. 9). The molecular weight of each population was estimated according to the elution volume. Based on the titration and size exclusion experiments, each Fc-binding protein can approximately bind about three IgG molecules. Accordingly, a molar ratio of Fc-binding protein to antibody of 1:3 was used to mix the Fc-binding protein and the antibodies.

Briefly, 90 μg of the anti-CD3 antibody or the anti-CD28 antibody was mixed with 10 μg of the Fc-binding protein. The mixed solution was sterile filtered and stored at 4° C. Optionally, the formed monospecific complexes were purified with a Superdex 200 column (GE Healthcare, Boston, MA). The elution peak of a complex was well separated from peaks of Fc-binding proteins or antibodies. The collected fractions of the complexes were quantified with a BCA protein assay kit (from Thermo Fisher Scientific, Waltham, MA) and the protein concentration was adjusted to 100-200 μg/ml.

Dual-specific complexes comprising both the anti-CD3 and anti-CD28 were also made by mixing the Fc-binding protein with the anti-CD3 antibody and anti-CD28 antibody. The anti-CD3 and anti-CD28 with equal concentrations (molarity) was mixed first. The antibody mixture was then mixed with the Fc-binding protein. It resulted in 50% of dual-specific complex, 25% of monospecific anti-CD3 complex and 25% of monospecific anti-CD28 complex. Briefly. 45 μg of the anti-CD3 and 45 μg of anti-CD28 antibodies were mixed thoroughly. About 10 μl of the Fc-binding protein was then added to the mixture. The complex solution was used for treating T cells.

Example 3: Expanding the T Cells

Since the number often increases in tens or hundreds of folds during in vitro/ex vivo expansion course, the T cells are regularly split when they are about 70-90% confluent. Splitting is done at ratio of about 1:2 to 1:5. The medium is replenished after a cell splitting. Additional T cell expanding agents can be introduced into the sub-cultures to compensate the dilution caused by the splitting.

Briefly, the T cells isolated from PBMC were collected, counted and equally dispensed into wells of a 48-well plate which was pre-blocked with HSA. Each well contained a starting number of 0.1×$10^6$ cells in a volume of 100 μL.

In one experiment, the wells were grouped based on the stimulation methods. Each group had three replicated wells which were treated equally. 3 μL of PBS was added to Group 1 (negative control). Group 2 was treated with 2 μL of anti-CD3 complex and 3 μL of anti-CD28 complex. Group 3 was treated with 3 μL of CTS Dynabeads CD3/CD28 (ThermoFisher) with a cell to bead ratio of about 1:3. Group 4 was treated with 3 μL of Immunocult CD3/CD28 (Stemcell Technologies Inc). Group 5 was treated with 5 μL of CD3/CD28 Streptamers Premix (IBA Lifesciences).

The T cells were sub-cultured in the presence of the expanding agents or PBS for 2 days before medium was changed. Fresh liquid T cell expanding agents were added immediately after medium change. The Dynabeads CD3/CD28 were kept with the cells during medium change. Cells were counted every two days after the splitting.

Figure 6:
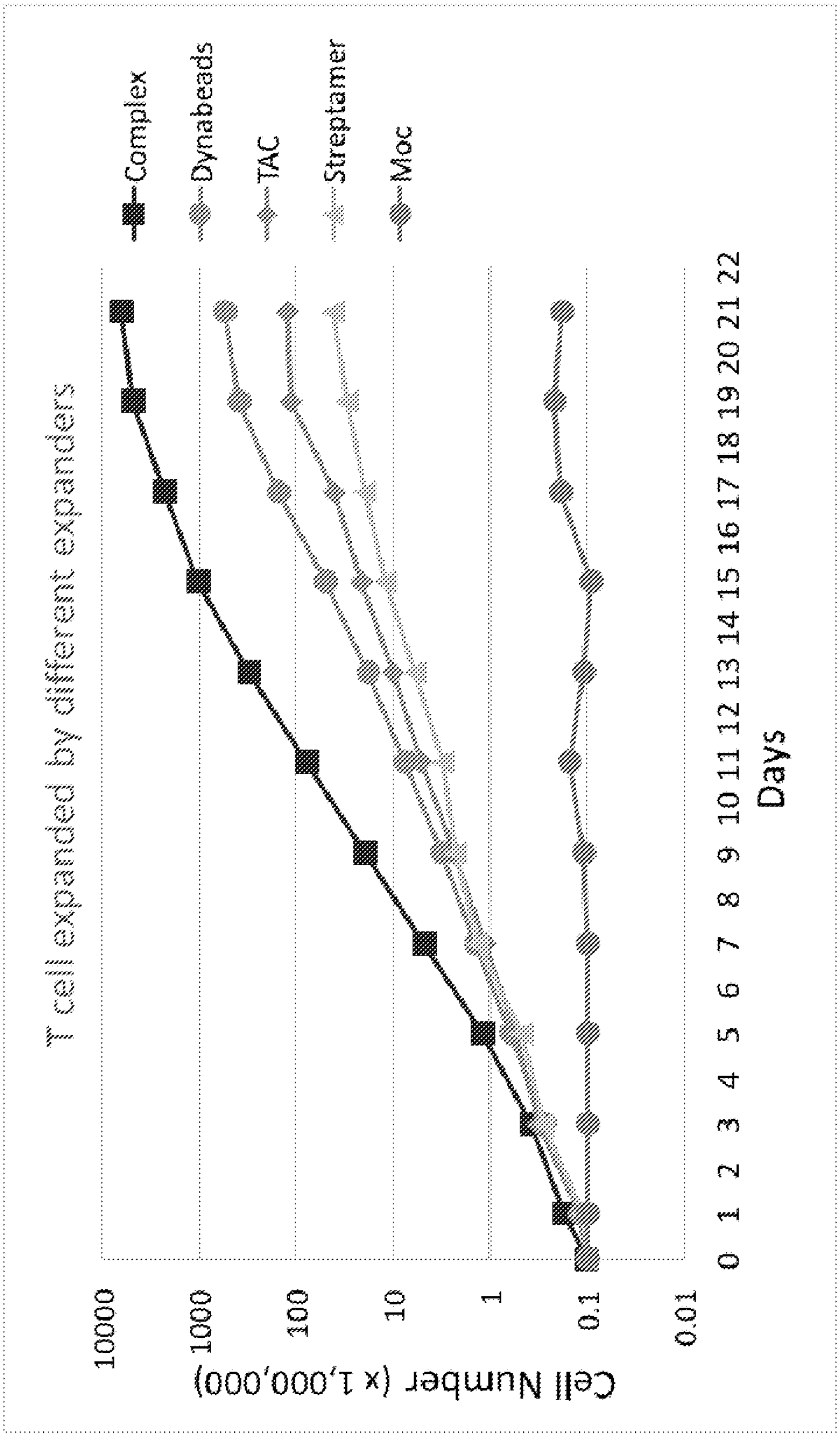
FIG. 6 is a graph showing the number of T cells that are expanded by the complexes, Dynabeads, ImmunoCult CD3/CD28 activator ("TAC"), and Streptamer CD3/CD28 Premix ("Streptamer"). The complexes include a monospecific anti-CD3 complex and a monospecific anti-CD28 complex, which were mixed at 1:2 ratio and added to the cell culture. The Dynabeads was added to the cells at beads to cells ratio of about 3:1. The immunoCult TAC and Streptamer Premix were added to the cell culture according to the protocol of manufacturers.

Results: As shown in FIG. 6, Group 2 which was treated with multi-protein complexes with CD3/CD28 showed much higher efficiency for expanding T cells. For comparison, the T cell expansion complexes was about 50% to 1,000% more efficient than the other expanding agents including Dynabeads CD3/CD28, Immunocult CD3/CD28 ("TAC") and CD3/CD28 Streptamers Premix ("Streptamer"). The starting population of the T cells was at about 0.1×$10^6$, and the cells were cultured in the presence of about 10 IU of IL-2. The cells were split and counted at 1-3 intervals. The cells that were treated with the complexes had a higher expanding rate than other tested agents.

TABLE 1

Fold of expansion with different expanding agents

| | Fold of Expansion | | |
|---|---|---|---|
| | Day 3 | Day 7 | Day 13 |
| Complexes | 3.8 | 48.1 | 3110.0 |
| Dynabeads | 2.8 | 14.2 | 182.3 |
| TAC | 3.2 | 12.3 | 106.1 |
| Streptamer | 2.7 | 13.6 | 59.7 |

Example 4: Viability of Cells Expanded by Different Expanding Agents

Figure 7:
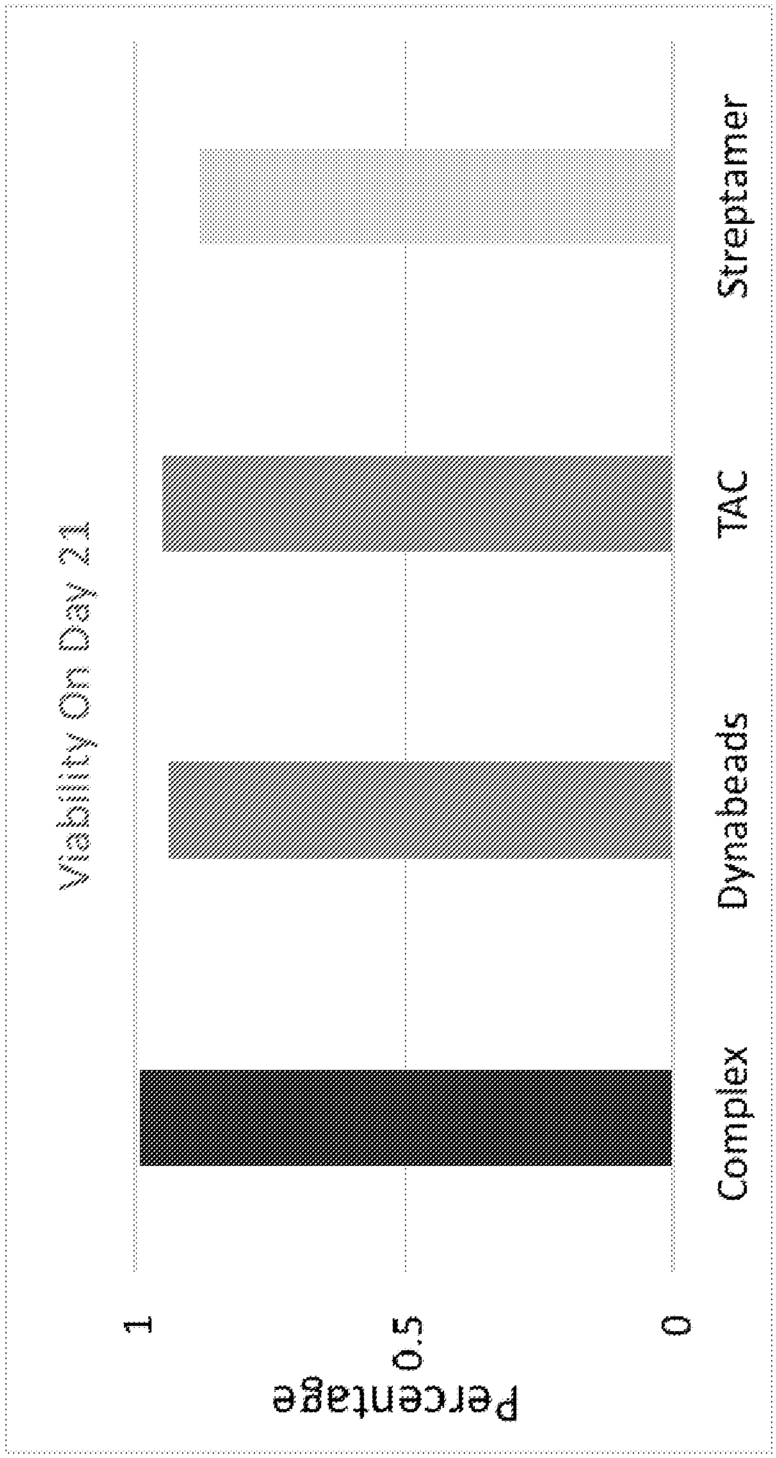
FIG. 7 is a graph showing the cell viability on Day 21 after expansion with the complexes, Dynabeads, TAC, and Streptamer CD3/CD28 Premix respectively. The T cells expanded by the complexes had over 99% of cell viability, the highest among all tested agents.

After 21 days of expansion, the T cells were stained with propidium iodide for viability test. As shown in FIG. 7, the viabilities of the cells expanded by the complexes, Dynabeads CD3/CD28, ImmunoCult CD3/CD28 activator and Streptamer CD3/CD28 Premix were 99.2%, 94.1%, 94.5% and 88.3%, respectively. Thus, the protein complexes did not cause significant T cell death after activation and expansion. In contrast, the T cells expended by other expanding agents had about 5-12% of cell death.

Example 5: CD4+ and CD8+ Population Analysis

The following fluorochrome-conjugated mAbs were used for flow cytometry analyses: FITC-conjugated anti-CD4, anti-CD8 (Dako Cytomation, Denmark), anti-CD3 (BD Biosciences, San José, CA) antibodies; PE-conjugated anti-CD4 antibody; PE-Cy-5-conjugated anti-CD8 antibody (Dako Cytomation, Denmark).

T cells were stained with FITC-conjugated or phycoerythrin (PE)-conjugated antibodies, including monoclonal mouse anti-human CD4 and CD8, a polyclonal goat anti-mouse antibody (Sigma, St. Louis, MO), and monoclonal mouse anti-human IgG, Fc fragment-specific F(ab)2 antibody (Jackson ImmunoResearch, West Grove, PA) was used for analysis of cell surface immuno-phenotypes.

Cells were washed and resuspended in 50 μL of Hanks buffered saline solution containing 2% FBS and 5 μL of stock antibody preparation. After a 10-min incubation at 4-10° C., cells were washed twice, resuspended in 300 μL of PBS containing 1% paraformaldehyde, and analyzed with a FACScan (BD Biosciences Immunocytometry Systems, San Jose, CA).

Figure 8:
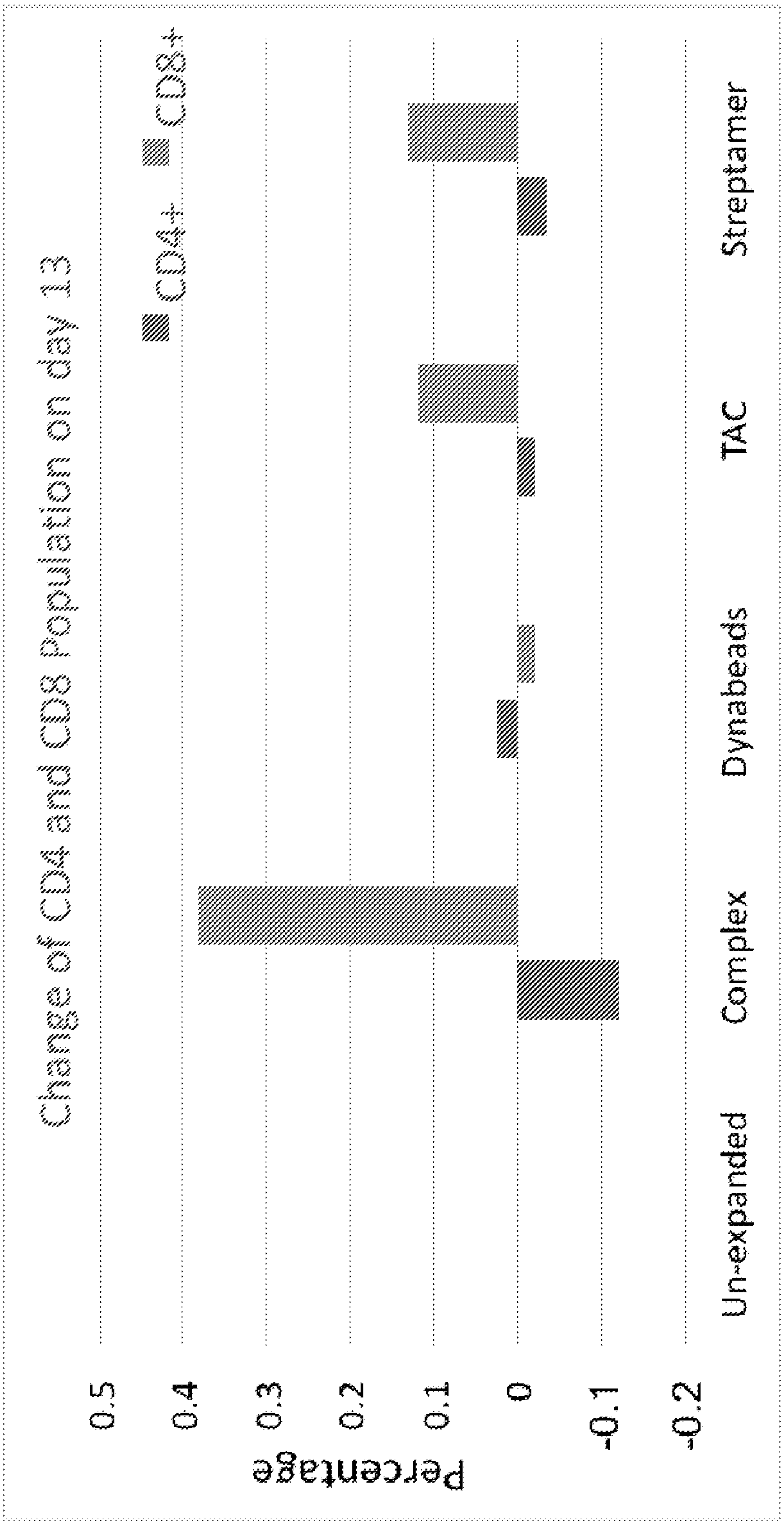
FIG. 8 is a graph showing fluorescence activated cell sorting (FACS) results in which T cells were stained with fluorescence labeled anti-CD3, anti-CD4 and anti-CD8 antibodies after isolation (Day 1, before agents were added), or after 13 days in culture with the complexex, Dynabeads, TAC or Streptamer CD3/CD28 Premix. The CD8+ population increased about 38% and the CD4+ population decreased about 12% when the T cells were treated with the complexes. The increase rate of CD8+ cells induced by the complexes was much higher that the increase rate in the other groups.

For each group, greater than 96% of the T cells expressed CD3. The ratio of $CD4^+$ and $CD8^+$ varied with different expanding agents as shown in FIG. 8 and the results are summarized in Table 2.

TABLE 2

The relative change of $CD4^+$ and $CD8^+$ populations

| | Population Percentage Changed | | | |
|---|---|---|---|---|
| | Complexes | Dynabeads | TAC | Streptamer |
| $CD4^+$ | −12.3% | +2.5% | −2.1% | −3.5% |
| $CD8^+$ | +38.1% | −2.2% | +11.9% | +13.1% |

The T cells expanded by the protein complexes had significantly higher CD8+ sub-population than other expanding agents. That indicates that the protein complexes can stimulate $CD8^+$ sub-population. Interestingly, the T cells expanded by the complexes, TAC, and Streptamer all had higher $CD8^+$ sub-population and lower CD4+ sub-population than the cells expanded by the Dynabeads.

Example 6: Functional Characters of Expanded T Cells

The T cells from PBMC are activated and expanded in the presence of two monomeric complexes (i.e. anti-CD3 complex and anti-CD28 complex) or Dynabeads CD3/CD28. Briefly, about 100 μL/well of T cells at the starting concentration of $0.1\times10^6$/mL are cultured with 100 IU/mL of IL-2. About 2 μL of the anti-CD3 monomeric complex and about 3 μL of anti-CD28 monomeric complex are added to the cells. Dynabeads CD3/CD28 expanding agent is used for comparison purpose. The beads are added to the cells at the final bead to cell ratio of 3:1. For the negative control, the wells are added with blank PBS.

After 13 days of expansion, the cells are collected, washed and passed to new wells without IL-2. The expanding agents or PBS are added. After 24 hours of cell growth, the supernatant of the cell culture is collected for analysis of the secreted cytokines.

Levels of IL-2, IL-4, INFγ and TNFα are measured by Enzyme Linked Immunosorbent Assay (ELISA). The patterns of cytokine secretion by the T cells depend on many factors including the sub-populations of the cells and the stimulatory conditions. The protein complexes and the magnetic bead expanding agent result in slightly different sub-populations of the T cells. And the different crosslinking effects on the CD3/CD28 molecules are likely to trigger different activation signaling inside the T cells. It is expected that the levels of the cytokines secreted by the T cells activated and expanded by the protein complexes and the Dynabeads are different.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for activating or expanding T cells, the method comprising contacting the T cells with a soluble multi-protein complex comprising a polypeptide comprising two or more Fc-binding domains, wherein each of the Fc-binding domains includes an engineered IgG-binding domain of Staphylococcal Protein A and has a sequence as set forth in SEQ ID NO: 6, and two or more Fc-containing proteins including an anti-CD3 antibody and an anti-CD28 antibody, each of the Fc-containing proteins comprising an Fc region, wherein each Fc-containing protein binds to the Fc-binding domain in the polypeptide by noncovalent interaction.

2. The method of claim 1, wherein the soluble multi-protein complex further comprises an anti-CD2 antibody, an anti-CD27 antibody, an anti-CD46 antibody or an anti-CD137 antibody, or a combination thereof.

3. A method for activating or expanding T cells, the method comprising contacting the T cells with a first soluble multi-protein complex comprising a first polypeptide comprising two or more Fc-binding domains, wherein each of the Fc-binding domains of the first polypeptide includes an engineered IgG-binding domain of Staphylococcal Protein A and has a sequence as set forth in SEQ ID NO: 6, and two or more anti-CD3 antibodies, wherein the anti-CD3 antibodies bind to the Fc-binding domain in the first polypeptide by noncovalent interaction, and a second soluble multi-protein complex comprising a second polypeptide comprising two or more Fc-binding domains, wherein each of the Fc-binding domains of the second polypeptide includes an engineered IgG-binding domain of Staphylococcal Protein A and has a sequence as set forth in SEQ ID NO: 6, and two or more anti-CD28 antibodies, wherein the anti-CD28 antibodies bind to the Fc-binding domain in the second polypeptide by noncovalent interaction.

4. The method of claim 3, the method further comprising contacting the T cells with a third soluble multi-protein complex comprising a third polypeptide comprising two or more Fc-binding domains, wherein each of the Fc-binding domains of the third polypeptide includes an engineered IgG-binding domain of Staphylococcal Protein A and has a sequence as set forth in SEQ ID NO: 6, and two or more Fc-containing proteins, each comprising an Fc region, wherein each Fc-containing protein binds to the Fc-binding domain in the third polypeptide, wherein the Fc-containing proteins are anti-CD2 antibodies, anti-CD27 antibodies, anti-CD28 antibodies, anti-CD46 antibodies or anti-CD137 antibodies.

* * * * *